(12) United States Patent
Jones et al.

(10) Patent No.: US 7,110,594 B2
(45) Date of Patent: Sep. 19, 2006

(54) MANIPULATING A DIGITAL DENTITION MODEL TO FORM MODELS OF INDIVIDUAL DENTITION COMPONENTS

(75) Inventors: Timothy N. Jones, Mountain View, CA (US); Muhammad Chishti, Sunnyvale, CA (US); Huafeng Wen, Redwood Shores, CA (US); Gregory P. Bala, San Jose, CA (US)

(73) Assignee: Align Technology, Inc., Santa Clara, CA (US)

( * ) Notice: Subject to any disclaimer, the term of this patent is extended or adjusted under 35 U.S.C. 154(b) by 608 days.

(21) Appl. No.: 10/099,310

(22) Filed: Mar. 12, 2002

(65) Prior Publication Data

US 2002/0102009 A1 Aug. 1, 2002

Related U.S. Application Data

(63) Continuation of application No. 09/311,941, filed on May 14, 1999, which is a continuation-in-part of application No. 09/264,547, filed on Mar. 8, 1999, which is a continuation-in-part of application No. 09/169,276, filed as application No. PCT/US98/12861 on Jun. 18, 1998, now abandoned.

(51) Int. Cl.
*G06K 9/00* (2006.01)
*A61C 3/00* (2006.01)
*A61C 11/00* (2006.01)
*A61C 9/00* (2006.01)

(52) U.S. Cl. ........................ 382/154; 433/24; 433/213; 433/214

(58) Field of Classification Search ................ 382/100, 382/128, 154; 345/419; 433/2, 24, 213, 433/214; 700/163; 348/77
See application file for complete search history.

(56) References Cited

U.S. PATENT DOCUMENTS

| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |

(Continued)

FOREIGN PATENT DOCUMENTS

AU          3031677          5/1979

(Continued)

OTHER PUBLICATIONS

Chiappone, "Constructing the Gnathologic Setup and Positioner", J. Clin. Orhod. vol. 14, No. 2, Feb. 1980, pp. 121-133.

(Continued)

*Primary Examiner*—Bhavesh M. Mehta
*Assistant Examiner*—John Strege
(74) *Attorney, Agent, or Firm*—Townsend and Townsend and Crew LLP

(57) ABSTRACT

A programmed computer is used to create a digital model of an individual component of a patient's dentition. The computer obtains a 3D digital model of the patient's dentition, identifies points in the dentition model that lie on an interproximal margin between adjacent teeth in the patient's dentition, and uses the identified points to create a cutting surface that separates portions of the dentition model representing the adjacent teeth.

18 Claims, 25 Drawing Sheets

U.S. PATENT DOCUMENTS

| | | | |
|---|---|---|---|
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |
| 4,575,330 A | 3/1986 | Hull | |
| 4,575,805 A | 3/1986 | Moermann et al. | |
| 4,591,341 A | 5/1986 | Andrews | |
| 4,609,349 A | 9/1986 | Cain | |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,836,778 A | 6/1989 | Baumrind et al. | |
| 4,837,732 A | 6/1989 | Brandestini et al. | |
| 4,850,864 A | 7/1989 | Diamond | |
| 4,850,865 A | 7/1989 | Napolitano | |
| 4,856,991 A | 8/1989 | Breads et al. | |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,935,635 A * | 6/1990 | O'Harra | 250/559.06 |
| 4,936,862 A | 6/1990 | Walker et al. | |
| 4,937,928 A | 7/1990 | van der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A | 10/1991 | Abbatte et al. | |
| 5,059,118 A | 10/1991 | Breads et al. | |
| 5,100,316 A | 3/1992 | Wildman | |
| 5,121,333 A | 6/1992 | Riley et al. | |
| 5,125,832 A | 6/1992 | Kesling | |
| 5,128,870 A | 7/1992 | Erdman et al. | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A | 9/1992 | Martz et al. | |
| 5,176,517 A | 1/1993 | Truax | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow | |
| 5,278,756 A | 1/1994 | Lemchen et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| RE35,169 E | 3/1996 | Lemchen et al. | |
| 5,518,397 A | 5/1996 | Andreiko et al. | |
| 5,528,735 A | 6/1996 | Strasnick et al. | |
| 5,533,895 A | 7/1996 | Andreiko et al. | |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Anderson et al. | |
| 5,605,459 A | 2/1997 | Kuroda et al. | |
| 5,607,305 A | 3/1997 | Anderson et al. | |
| 5,621,648 A | 4/1997 | Crump | |
| 5,645,420 A | 7/1997 | Bergersen | |
| 5,645,421 A | 7/1997 | Slootsky | |
| 5,655,653 A | 8/1997 | Chester | |
| 5,671,136 A | 9/1997 | Willholt, Jr. | |
| 5,683,243 A | 11/1997 | Andreiko et al. | |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A * | 1/1999 | van Nifterick et al. | 433/213 |
| 5,866,058 A | 2/1999 | Batchelder et al. | |
| 5,879,158 A | 3/1999 | Doyle et al. | |
| 5,880,961 A | 3/1999 | Crump | |
| 5,880,962 A | 3/1999 | Andersson et al. | |
| 5,934,288 A * | 8/1999 | Avila et al. | 600/443 |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 6,015,289 A | 1/2000 | Andreiko et al. | |
| 6,044,309 A | 3/2000 | Honda | |
| 6,049,743 A | 4/2000 | Baba | |
| 6,062,861 A * | 5/2000 | Andersson | 433/213 |
| 6,068,482 A | 5/2000 | Snow | |
| 6,099,314 A * | 8/2000 | Kopelman et al. | 433/213 |
| 6,123,544 A | 9/2000 | Cleary | |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,217,334 B1 | 4/2001 | Hultgren | |
| 6,244,861 B1 | 6/2001 | Andreiko et al. | |
| 6,309,215 B1 | 10/2001 | Phan et al. | |
| 6,315,553 B1 | 11/2001 | Sachdeva et al. | |
| 6,322,359 B1 * | 11/2001 | Jordan et al. | 433/73 |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,409,504 B1 | 6/2002 | Jones et al. | |
| 6,524,101 B1 | 2/2003 | Phan et al. | |
| 6,549,200 B1 * | 4/2003 | Mortlock et al. | 345/419 |
| 6,554,611 B1 | 4/2003 | Chishti et al. | |
| 2002/0006597 A1 | 1/2002 | Andreiko et al. | |

FOREIGN PATENT DOCUMENTS

| | | |
|---|---|---|
| AU | 517102 | 7/1981 |
| AU | 5598894 | 6/1994 |
| CA | 1121955 | 4/1982 |
| DE | 2749802 | 5/1978 |
| DE | 69327661 | 7/2000 |
| EP | 0091876 | 10/1983 |
| EP | 0299490 | 1/1989 |
| EP | 376873 A2 | 7/1990 |

| | | | |
|---|---|---|---|
| EP | 490848 B1 | 6/1992 | |
| EP | 774933 B1 | 5/1997 | |
| EP | 541500 A1 | 6/1998 | |
| EP | 731673 B1 | 9/1998 | |
| ES | 463897 | 1/1980 | |
| FR | 2369828 | 6/1978 | |
| FR | 2652256 | 3/1991 | |
| GB | 1550777 | 8/1979 | |
| JP | 53-058191 | 5/1978 | |
| JP | 04-028359 | 1/1992 | |
| JP | 08-508174 | 9/1996 | |
| WO | WO 90/08512 A1 | 8/1990 | |
| WO | WO 91/04713 A1 | 4/1991 | |
| WO | WO 94/10935 A1 | 5/1994 | |
| WO | WO 98/32394 | 7/1998 | |
| WO | WO 98/44865 A1 | 10/1998 | |
| WO | WO 98/58896 A1 | 12/1998 | |

OTHER PUBLICATIONS

Cottingham, "Gnathologic Clear Plastic Positioner", Am. J. Orthod. vol. 55, No. 1, Jan. 1969, pp. 23-31.
Cureton, "Correcting Maligned Mandibular Incisors with Removable Retainers", J. Clin. Orthod. vol. 30, No. 7, Jul. 1996, pp. 390-395.
Elsasser, Some Observations on the History and Uses of the Kesling Positioner, Am. J. Orthod. vol. 36, Jan. 12, 1950, pp. 386-374.
Kamada et al., "Construction of Tooth Positioners with LTV Vinyl Silicone Rubber and some case Reports", J. Nihon University School of Dentistry, vol. 24, No. 1, Mar. 1982, pp. 1-27.
Kesling, The Philosophy of the Tooth Positioning Appliance, Am. J. Orthod. Oral Surg. vol. 31, No. 6, Jun. 1945, pp. 297-304.
Kesling, "Coordinating the Predetermined Pattern and Tooth Positioner with Conventional Treatment", Am. J. Orthod. Oral Surg. vol. 32, No. 5, May 1946.
Kleeman et al., "The Speed Positioner", J. Clin. Orthod. vol. 30, No. 12, Dec. 1996, pp. 673-680.
Kuroda et al., "Three Dimensional Dental Cast Analyzing System Using Laser Scanning," Am. J. Orthod. Dentofac. Orthop., vol. 110, No. 4, Oct. 1996, pp. 365-369.
Nishiyama et al., "A New Construction of Tooth Positioner by LTV Vinyl Silicone Rubber", J. Nihon Univ. School of Dentistry, vol. 19, No. 2, Jun. 1977, pp. 93-102.
Shilliday, Minimizing Finishing Problem's with the Minipositioner, Am. J. Orthod. vol. 69, No. 6, Jun. 1971, pp. 596-599.
Warunek et al. "Physical and Mechanical Properties of Elastomers in Orthodontic Positioners," Am. J. Orthod. Dentofac. Orthop., vol. 95, No. 5, May 1989, pp. 388-400.
Alexander et al., "The DigiGraph Work Station Part 2, Clinical Management," JCO (Jul. 1990), pp. 402-407.
Altschuler et al., "Laser Electro-Optic System for Rapid Three-Dimensional (3D) Topographic Mapping of Surfaces," Optical Engineering, vol. 20(6) (1981), pp. 953-961.
Altschuler et al, "Measuring Surfaces Space-Coded by a Laser-Projected Dot Matrix," SPIE Imaging Applications for Automated Industrial Inspection and Assembly, vol. 182 (1979), p. 187-191.
American Association for Dental Research, Summary of Activities, Mar. 20-23, 1980, Los Angeles, CA, p. 195.
Andersson et al., "Clinical Results with Titanium Crowns Fabricated with Machine Duplication and Spark Erosion," Acta Odontological Scandinavia, vol. 47 (1989), pp. 279-286.
Baumrind et al., "A stereophotogrammetric system for the detection of prosthesis loosening in total hip arthroplasty, Applications of Human Biostereometrics (NATO)," Proceedings of the Society of Photo-Optical Instrumentation Engineers, vol. 166, Jul. 9-13, 1978, pp. 112-123.
Baumrind et al., Mapping the Skull in 3-D, Reprinted from The Journal, California Dental Association, vol. 48, No. 2 (1972 Fall Issue) 11 pages total.
Baumrind et al., "Seminars in Orthodontics," Seminars in Orthodontics, vol. 7, No. 4 (Dec. 2001), p. 222.
Baumrind, "A System for Craniofacial Mapping Through the Integration of Data from Stereo X-Ray Films and Stereo Photographs,"
An invited paper submitted to the 1975 American Society of Photogram, Symposium on Close-Range Photogram. Systems, University of Ill, Aug. 26-30, 1975, pp. 1-25.
Baumrind, "Integrated Three-Dimensional Craniofacial Mapping: Background, Principles, and Perspectives," Seminars in Orthodontics, vol. 7, No. 4 (Dec. 2001), pp. 223-232.
Bhatia et al., "A Computer-Aided Design for Orthognathic Surgery," British Journal of Oral and Maxillofacial Surgery, vol. 22 (1984), pp. 237-253.
Biggerstaff et al., "Computerized analysis of occlusion in the postcanine dentition," American Journal of Orthodontics, vol. 61, No. 3 (Mar. 1972), pp. 245-254.
Biggerstaff, "Computerized Diagnostic Setups and Simulations," The Angle Orthodontist, vol. 40, No. 1 (Jan. 1970), pp. 28-36.
Brandestini et al., "Computer Machined Ceramic Inlays: In Vitro Marginal Adaptation," Journal of Dental Research, vol. 64/Special Issue/Abstract, IADR/AADR Abstracts 1985, 1 page total.
Brook et al., An Image Analysis System for the Determination of Tooth Dimensions from Study Casts: Comparison with Manual Measurements of Mesio-distal Diameter, Abstract of Papers, 1985, Dept. of Children's Dentistry and Orthodontics, J Dent Res., Mar. 1986, pp. 428-431.
Burstone (interview), "Dr. Charles J. Burstone on The Uses of the Computer in Orthodontic Practice (Parts1 and 2)," Journal of Clinical Orthodontics, (Part 1) vol. 8, No. 7 , Jul. 1979; (Part 2) vol. 8, No. 8 pp. 539-551, Aug. 1979.
Burstone et al., "Precision adjustment of the transpalatal lingual arch: Computer arch from predetermination," Am. Journal of Orthodontics, vol. 79, No. 2 (Feb. 1981), pp. 115-133.
Chaconas et al., "The DigiGraph Work Station, Part 1, Basic Concepts," JCO (Jun. 1990), pp. 360-367.
Chafetz et al., "Subsidence of the Femoral Prosthesis, A Stereophotogrammetric Evaluation," Clinical Orthopaedics and Related Research, No. 201 (Dec. 1985), pp. 60-67.
Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, Canadian Dental Journal, vol. 54(9), ,(1988), pp. 661-666.
Crawford, "CAD/CAM in the Dental Office: Does It Work?" Canadian Dental Journal, vol. 57, No. 2 (Feb. 1991), pp. 121-123.
Crooks, "CAD/CAM Comes to USC," USC Dentistry, (Spring 1990) pp. 14-17.
Curry et al., "Integrated Three-Dimensional Craniofacial Mapping at the Craniofacial Research Instrumentation Laboratory/University of the Pacific," Seminars in Orthodontics, vol. 7, No. 4 (Dec. 2001), pp. 258-265.
Cutting et al., "Three-Dimensional Computer-Assisted Design of Craniofacial Surgical Procedures: Optimization and Interaction with Cephalometric and CT-Based Models," Plastic and Reconstructive Surgery, vol. 77, No. 6 (Jun. 1986), pp. 877-885.
DCS Dental AG, "The CAD/CAM 'DCS Titan System' for Production of Crowns/Bridges" DSC Production AG, Jan. 1992, pp. 1-7.
Defranco et al., "Three-Dimensional Large Displacement Analysis of Orthodontic Appliances," J. Biomechanics, vol. 9 (1976), pp. 793-801.
Dental Institute University of Zurich Switzerland, Program for International Symposium on Computer Restorations: State of the Art of the CEREC-Method, May 1991, 3 pages total.
DenTrac Corporation, Dentrac document, pp. 4-13.
Duret et al, "CAD-CAM in Dentistry," Journal of the American Dental Association, vol. 117 (Nov. 1988), pp. 715-720.
Duret et al., "CAD/CAM imaging in dentistry," Current Opinion in Dentistry, vol. 1 (1991), pp. 150-154.
Duret, "The Dental CAD/CAM, General Description of the Project," Hennson International Product Brochure, Jan. 1986., 18 pages total.
Economides, "The Microcomputer in the Orthodontic Office," JCO, (Nov. 1979), pp. 767-772.
Faber et al.,"Computerized interactive orthodontic treatment planning," Am. J. Orthod., vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., Accuracy of Cephalometric Prediction in Orthognathic Surgery, Abstract of Papers, *Journal of Dental Research*, vol. 70 (1987), pp. 754-760.

Grayson, "New Methods for Three Dimensional Analysis of Craniofacial Deformity," Symposium: Computerized Facial Imaging in Oral and Maxilofacial Surgery, AAOMS Sep. 13, 1990, 3 pages total.

Guess et al., Computer Treatment Estimates in Orthodontics and Orthognathic Surgery, *JCO*, (Apr., 1989), pp. 262-28.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

Inside the ADA, *Journal Of The American Dental Assoc.*, vol. 118 (Mar. 1989) 9 pages total.

JCO Interviews, "Craig Andrelko, DDS, MS on the Elan and Orthos Systems", JCO, (Aug. 1994), pp. 459-468.

JCO Interviews, "Dr. Horner W. Phillips on Computers in Orthodontic Practice, Part 2," JCO, (Dec. 1983), pp. 819-831.

Jerrold, "The problem, electronic data transmission and the law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case reports on tooth positioners using LTV vinyl silicone rubber" J. Nihon University School of Dentistry, 26(1):11-29, 1984.

Kanazawa et al., "Three-Dimensional Measurements of the Occlusal Surfaces of Upper Molars in a Dutch Population," *J. Dent Res.*, vol. 63, No. 11 (Nov. 1984), pp. 1298-1301.

Leinfelder et al., "A new method for generating ceramic restorations: a CAD-CAM system," *Journal Of The American Dental Assoc.*, vol. 118, No. 6 (Jun. 1989), pp. 703-707.

McNamara et al., *Orthodontic and Orthopedic Treatment in the Mixed Dentition*, Needham Press, Jan. 1993. pp. 347-353.

McNamara et al., "Invisible Retainers", *J. Clinical Orthodontics*, (Aug. 1985) pp. 570-578.

Mörmann et al., Marginal Adaptation von adhasiven Porzellaninlays in vitro, *Schwizerische Monatsshrift fur Zahnmedizin*, vol. 85 (1985), p. 1118-1129.

Nahoum, "The vacuum formed dental contour appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Pinkham, "'Foolish' Concept Propels Technology," *Dentist*, Jan./Feb. 1989, 3 pages total.

Ponitz, Invisible Retainers, 59 *Am. J. Orthodontics*, Mar. 1971, pp. 266-272.

Procera Research Projects, *PROCERA Research Projects 1993—Abstract Collection*, 1993, pp. 3-28.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The development of a 3D Cast Analysis System," *British Journal of Orthodontics*, pp. 53-54.

Richmond, "Recording the dental cast in three dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computer Tomography in Maxillofacial Surgical Planning," *Arch Otolamgol Head Neck Surg.* vol. 114 (Apr. 1988), pp. 438-442.

Segu et al., "Computer-aided Cefalometry and New Mechanics in Orthodontics" (Article Summary in English, article in German), *Fortschr. Koeferothop.* 44, 370-376 (Nr. 5), 1983.

Siemens, CEREC—Computer-Reconstruction, High Tech in der Zahnmedizin, 14 page total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 21 pages total.

U..S. Department of Commerce, National Technical Information Service, "Holodontograpy: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Varady et al., "Reverse Engineering of Geometric Models—An Introduction," May 13, 1996, pp. 1-28.

Warunek et al., "Clinical use of silicone elastomer appliances" *JCO*, MH (10):694-700, 1989.

Williams, Dentistry and CAD/CAM: Another French Revolution, *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, New Advances in Personal Computer Applications for Cephalometric Analysis, Growth Prediction, Surgical Treatment Planning and Imaging Processing, Symposium: Computerized Facial Imaging in Oral and Maxilofacial Surgery, AAOMS, Sep. 13, 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical measurement of dental cast profile and application to analysis of three-dimensional tooth movement in orthodontics," *Frontiers in Med. and Biol. Eng'g*, vol. 1, No. 2 (1988), pp. 119-130.

Biostar Opeation & Training Manual. Great Lakes Orthodontics, Ltd. 199 Fire Tower Drive, Tonawanda, New York, 14150-5890, 20 pages total.

Wells, Application of the Positioner Appliance in Orthodontic Treatment, *Am. J. Orthodont*, (1970) 58:351-366.

Yoshii, Research on a New Orthodontic Appliance: The Dynamic Positioner (D.P.)-1. The D.P. concept and Implementation of Transparent Silicone Resin (Orthocon), *Nippon Dental Review*, vol. 452,Jun. 1980, pp. 61-74.

Yoshii, Research on A New Orthodontic Appliance: The Dynamic Positioner (D.P.)-II. Th D.P. Manufacturing Procedure and Clinical Applications, *Nippon Dental Review*, vol. 454, Aug. 1980, pp. 107-130.

Yoshii, Research on a New Orthodontic Appliance: The Dynamic Positioner (D.P.)-III-The General Concept of the D.P. Method and its Therapeutic Effect, Part 2. Skeletal reversed Occlusion Case Reports, *Nippon Dental Review*, vol. 458, Dec. 1980, pp. 112-129.

Yoshii, Research on a New Orthodontic Appliance: The Dynamic Positioner (D.P.)-III. The General Concept of the D.P. Method and its Therapeutic Effect, Part 1, Dental and Functional Reversed Occlusion Case Reports, *Nippon Dental Review*, vol. 457, Nov. 1980, pp. 146-164.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler, 3D Mapping of Maxillo-Facial Prosthesis, AADR Abstract #607,1980, 2 pages total.

Andrews, *The Six Keys to Optimal Occlusion Straight Wire*, Chapter 3, pp. 13-24.

Begole et al., A Computer System for the Analysis of Dental Casts, *The Angle Orthodontist*, vol. 51 No. 3 (Jul. 1981), pp. 253-259.

Bernard et al., Computerized Diagnosis in Orthodontics for Epidemiological Studies: A Progress Report, Paper presented at International Association for Dental Research 66th General Session, Mar. 9-13, 1988, Montreal, Canada. The abstract is published in *J Dental Res Special Issue* vol. 67, p. 169.

Boyd et al., Three Dimensional Diagnosis and Orthodontics Treatment of Complex Malocclusions Wlith the Invisalign Appliance, *Seminars in Orthodontics*, vol. 7, No. 4 (Dec. 2001), p. 274-293.

Cardinal Industrial Finishes, Powder Coatings information posted at http://www.cardinalpaint.com on Aug. 25, 2000, 2 pages total.

DENT-X posted at http://www.dent-x.com/DentSim.htm Sep. 24, 1998,6 pages total.

Doyle, Digital Dentistry, *Computer Graphics World*, Oct. 2000 pp. 50-52, 54.

Duret, Vers Une Prosthese Informatisee, (English translation also attached), *Tonus*, vol. 75, (Nov. 15, 1985), pp. 55-57.

Fütterling et al., "Automated Finite Element Modeling of a Human Mandible with Dental Implants," *WSCG '98 -Conference Program*, retrieved from the Internet: <<http://wscg.zcu.cz/wscg98/papers98/Strasser_98.pdf.>>, 8 pages total.

Gottleib et al., JCO Interviews Dr. James A. McNamura, Jr., on the Frankel Appliance: Part 2: Clinical Management, *Journal of Clinical Orthodonitcs*, vol. 16, No. 6, (Jun. 1982) pp. 390-407.

Heaven et al., Computer-based Image Analysis of Artificial Root Surface Caries, Abstracts of Papers, *Journal of Dental Research*, vol. 70,Apr. 17-21, 1991, p. 528.

Hojjatie et al., "Three-Dimensional Finite Element Analysis of Glass-Ceramic Dental Crowns," *J Biomech.* (1990) vol. 23, No. 11, pp. 1157-1166.

Kunii et al., Articulation Simulation for an Intelligent Dental Care System, *Displays* (1994) 15:181-188.

Laurendeau et al, A Computer-Vision Technique for the Acquisition and Processing of 3-D Profiles of Dental Imprints: An Application in Orthodontics, IEEE Transactions on Medical Imaging, vol. 10, No. 3 (Sep. 1991), pp. 453-461.

Manetti et al., Computer-aided Cefalometry and New Mechanics in Orthodontics (Article Summary in English, article in German), *Fortschr. Kieferothop.* 44, 370-376 (Nr. 5), 1983.

McCann, Inside the ADA, *Journal Of The American Dental Assoc*, vol. 118 (Mar. 1989) pp. 286-294.

Moermann et al, Computer Machined Adhesive Porcelain Inlays: Margin Adaptation after Fatigue Stress, IADR Abstract 339, *Journal of Dental Research*, vol. 66(a) (1987), p. 763.

Mörmann et al., "Marginale Adaptation von adhäsuven Porzelianinlays in vitro," Separatdruck aus: Schweiz. Mschr. Zahnmed. 95: 1118-1129, 1985.

Nishiyama et al., A New Construction of Tooth Repositioner by LTV Vinyl Silicone Rubber, J. Nihon University of Dentistry (1977) 19(2):93-102.

Pinkham, Inventor's CAD/CAM May Transform Dentistry, *Dentist*, Sep. 1990, 3 pages total.

Tru-Tain Orthodontic & Dental Supplies, Product Brochure, Rochester, Minnesota 55902, 16 pages total.

Proffit et al., *Contemporary Orthodontics* (Second Ed.) Chapter 15, Mosby Inc, (Oct. 1992 ), pp. 470-533.

Raintree Essix & Ars Materials, Inc., Raintree Essix, Technical Magazine Table of contents and Essix Appliances, httpz;// www.essix.com/magazine/default.html Aug. 13, 1997, 7 pages.

Redmond et al. Clinical Implications of Digital Orthodontics, *Am. J. Orthodont. Dentofacial Orthopedics*, vol. 117 No. 2 (2001), pp. 240-242.

Rekow et al., "CAD/CAM for Dental Restorations—Some of the Curious Challenges," *IEEE Transactions on Biomedical Engineering*, (Apr. 1991) vol. 38, No. 4, pp. 344-345.

Rekow et al., "Comparison of Three Data Acquisition Techniques for 3-D Tooth Surface Mapping," *Annual International Conference of the IEEE Engineering in Medicine and Biology Society*, (1991) vol. 13, No. 1, pp. 344-345.

Richmond et.al., The Development of the PAR Index (Peer Assessment Rating): Reliability and Validity, *European Journal of Orthodontics* (1992) 14:125-139.

Schroeder et al., Eds., The Visual Toolkit, Prentice Hall PTR, New Jersey (1998) Chapters 6, 8 & 9, (pp. 153-210,309-354, and 355-428, respectively).

Sinclair, "The Readers' Corner," *Journal of Clinical Orthodontics*, vol. 26, No. 6, (Jun. 1992) pp. 369-372.

Van der Linden et al., Three-Dimensional Analysis of Dental Casts by Means of the Optocom, *J Dent Res*, Jul.-Aug. 1972, p. 1100.

\* cited by examiner

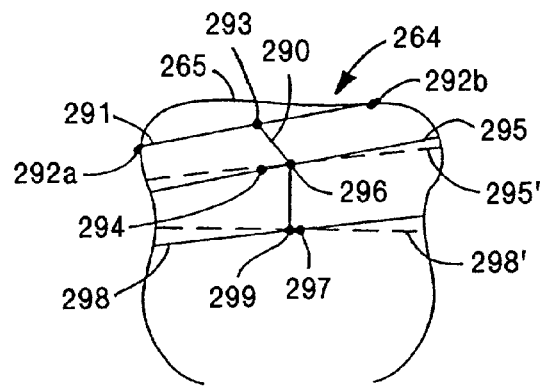
FIG. 17
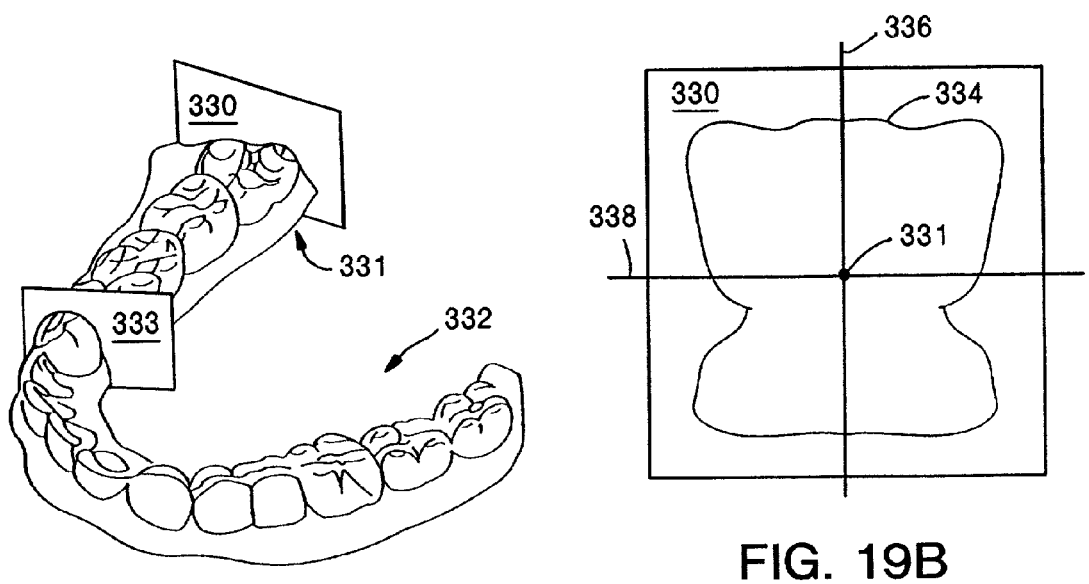
FIG. 19A
FIG. 19B

MANIPULATING A DIGITAL DENTITION MODEL TO FORM MODELS OF INDIVIDUAL DENTITION COMPONENTS

CROSS-REFERENCES TO RELATED APPLICATIONS

This application is a continuation of U.S. patent application Ser. No. 09/311,941 filed May 14, 1999, which was continuation-in-part of U.S. patent application Ser. No. 09/264,547, filed on Mar. 8, 1999, which was a continuation-in-part of U.S. patent application Ser. No. 09/169,276 filed on Oct. 8, 1998, (now abandoned) which is a 371 of PCT application PCT/US98/12861 (WO98/58596 published Dec. 12, 1998), filed on Jun. 8, 1998, which claimed priority from U.S. patent application Ser. No. 08/947,080 filed on Oct. 8, 1997, which claimed priority from U.S. provisional application No. 60/050,342 filed on Jun. 20, 1997, the full disclosures of which are incorporated herein by reference.

BACKGROUND OF THE INVENTION

The invention relates to the fields of computer-assisted dentistry and orthodontics. Two-dimensional (2D) and three-dimensional (3D) digital image technology has recently been tapped as a tool to assist in dental and orthodontic treatment. Many treatment providers use some form of digital image technology to study the dentitions of patients. U.S. patent application Ser. No. 09/169,276 describes the use of 2D and 3D image data in forming a digital model of a patient's dentition, including models of individual dentition components. Such models are useful, among other things, in developing an orthodontic treatment plan for the patient, as well as in creating one or more orthodontic appliances to implement the treatment plan.

BRIEF SUMMARY OF THE INVENTION

The inventors have developed several computer-automated techniques for subdividing, or segmenting, a digital dentition model into models of individual dentition components. These dentition components include, but are not limited to, tooth crowns, tooth roots, and gingival regions. The segmentation techniques include both human-assisted and fully-automated techniques. Some of the human-assisted techniques allow a human user to provide "algorithmic hints" by identifying certain features in the digital dentition model. The identified features then serve as a basis for automated segmentation. Some techniques act on a volumetric 3D image model, or "voxel representation," of the dentition, and other techniques act on a geometric 3D model, or "geometric representation."

In one aspect, the invention involves obtaining a three-dimensional (3D) digital model of a patient's dentition and analyzing the model to determine the orientation of at least one axis of the model automatically. In some implementations, the model's z-axis is found by creating an Oriented Bounding Box (OBB) around the model and identifying the direction in which the OBB has minimum thickness. The z-axis extends in this direction, from the model's bottom surface to its top surface. Moreover, in a dentition model having only one mandible, one of the model surfaces is substantially flat and an opposite surface is textured. The direction of the positive z-axis can be identified in this type of model by identifying which of the surfaces is flat or textured. One technique for doing so involves creating one or more planes that are roughly normal to the z-axis and then creating line segments that extend between the planes and the top and bottom surfaces of the dentition model. The surface for which all of the line segments are of one length is identified as being the flat surface, and the surface for which the line segments have varying lengths is identified as being the textured surface.

In other implementations, the x- and y-axes are found by selecting a two-dimensional (2D) plane that contains the axes and an arch-shaped cross section of the dentition model and identifying the orientations of the axes in this plane. In general, the arch-shaped cross section is roughly symmetrical about the y-axis. One technique for identifying the y-axis involves identifying a point at each end of the arch-shaped cross section, creating a line segment that extends between the identified points, and identifying the orientation of the y-axis as being roughly perpendicular to the line segment. The point at each end of the arch can be identified by selecting a point that lies within an area surrounded by the arch-shaped cross section, creating a line segment that extends between the selected point and an edge of the 2D plane, sweeping the line segment in a circular manner around the selected point, and identifying points at the ends of the arch-shaped cross section at which the sweeping line segment begins intersecting the cross section of the dentition model and stops intersecting the cross section of the dentition model. In general, the x-axis is perpendicular to the y-axis.

In another aspect, the invention involves using a programmed computer to create a digital model of an individual component of a patient's dentition by obtaining a 3D digital model of the patient's dentition, identifying points in the dentition model that lie on an inter-proximal margin between adjacent teeth in the patient's dentition, and using the identified points to create a cutting surface for use in separating portions of the dentition model representing the adjacent teeth.

In some implementations, 2D cross sections of the dentition model are displayed to a human operator, and the operator provides input identifying approximate points at which the interproximal margin between the adjacent teeth meets gingival tissue. In some cases, the dentition model includes a 3D volumetric model of the dentition, and the input provided by the operator identifies two voxels in the volumetric model. The computer then defines a neighborhood of voxels around each of the two voxels identified by the human operator, where each neighborhood includes voxels representing the dentition model and voxels representing a background image. The computer selects the pair of voxels, one in each neighborhood, representing the background image that lie closest together.

In some of these implementations, the computer also identifies voxels on another 2D cross section that represent the interproximal margin. One technique for doing so is by defining a neighborhood of voxels around each of the selected voxels, where each neighborhood includes voxels representing the dentition model and voxels representing a background image, projecting the neighborhoods onto the other 2D cross section, and selecting two voxels in the projected neighborhoods that represent the inter-proximal margin.

In another aspect, the invention involves displaying an image of a dentition model, receiving input from a human operator identifying points in the image representing a gingival line at which a tooth in the dentition model meets gingival tissue, and using the identified points to create a cutting surface for use in separating the tooth from the gingival tissue in the dentition model. The cutting surface often extends roughly perpendicular to the dentition's occlusal plane.

In some implementations, the cutting surface is created by projecting at least a portion of the gingival line onto a plane that is roughly parallel to the occlusal plane and then creating a surface that connects the gingival line to the projection. One way of establishing the plane is by fitting the plane among the points on the gingival line and then shifting the plane away from the tooth in a direction that is roughly normal to the plane. For example, the plane can be shifted along a line segment that includes a point near the center of the tooth and that is roughly perpendicular to the plane. The length of the line segment usually approximates the length of a tooth root.

In other embodiments, the cutting surface extends roughly parallel to the dentition's occlusal plane in the dentition model. In some of these embodiments, the input received from the human operator identifies points that form two 3D curves representing gingival lines at which teeth in the dentition model meet gum tissue on both the buccal and lingual sides of the dentition model. The cutting surface is created by fitting a surface among the points lying on the two curves. For each tooth, a point lying between the two curves is identified and surface triangles are created between the identified point and points on the two curves. One technique for identifying the point involves averaging, for each tooth, x, y and z coordinate values of the points on portions of the two curves adjacent to the tooth.

Other embodiments involve creating, for each tooth, a surface that represents the tooth's roots. One technique for doing so involves projecting points onto a plane that is roughly parallel to the occlusal plane and connecting points on the two curves to the projected points. The surface can be used to separate portions of the dentition model representing the tooth roots from portions representing gingival tissue. The model of the tooth roots is then connected to the tooth model.

Other embodiments and advantages are apparent from the detailed description and the claims below.

BRIEF DESCRIPTION OF THE DRAWINGS

FIG. 17 is a horizontal 2D cross section of a dentition model illustrating a curve creation technique for use with the arch curve fitting technique.

FIGS. 19A and 19B are a perspective view and a vertical 2D cross-sectional view of a dentition model illustrating another technique for use in segmenting the dentition model.

FIG. 24 is a flowchart for the gingival margin detection technique.

DETAILED DESCRIPTION OF THE INVENTION

Figure 1A:
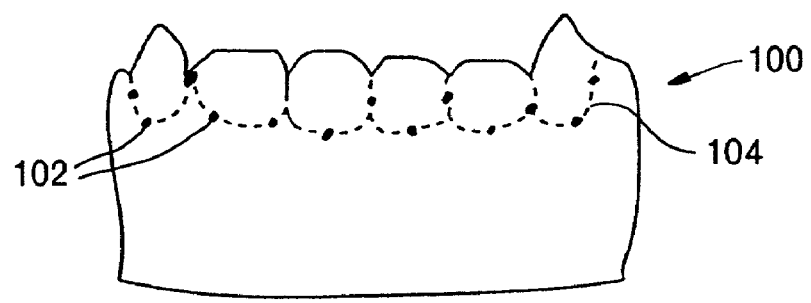
FIGS. 1A, 1B, and 2 are partial views of a dentition model as displayed on a computer monitor and segmented with a human-operated saw tool.

U.S. patent application Ser. No.09/169,276 describes techniques for generating a 3D digital data set that contains a model of a patient's dentition, including the crowns and roots of the patient's teeth as well as the surrounding gum tissue. One such technique involves creating a physical model of the dentition from a material such as plaster and then digitally imaging the model with a laser scanner or a destructive scanning system. These techniques are used to produce a digital volumetric 3D model ("volume element representation" or "voxel representation") of the dentition model, and/or a digital geometric 3D surface model ("geometric model") of the dentition. The computer-implemented techniques described below act on one or both of these types of 3D dentition models.

In creating a voxel representation, the physical model is usually embedded in a potting material that contrasts sharply with the color of the physical model to enhance detection of the dentition features. A white dentition model embedded in a black potting material provides the sharpest contrast. A wide variety of information can be used to enhance the 3D model, including data taken from photographic images, 2D and 3D x-rays scans, computed tomography (CT) scans, and magnetic resonance imaging (MRI) scans of the patient's dentition.

The 3D data set is loaded into a computer which, under control of a program implementing one or more techniques of the dentition, either with or without human assistance, segments the digital dentition model into digital models of individual dentition components, such as teeth and gingival tissue. In one implementation, the computer produces a digital model of each individual tooth in the patient's dentition, as well as a digital model of the gingival tissue surrounding the teeth.

To segment the digital dentition model accurately, the computer often must know the exact orientation of the dentition model. One technique for establishing the orientation of the digital dentition model in the 3D data set involves holding the physical dentition model at a prescribed orientation during the digital imaging process discussed above. Embedding the physical model at a particular orientation in a solid potting material is one way of holding the physical model. In some systems, however, even this technique introduces small errors in the orientation of the dentition model.

Orienting the Digital Dentition Model

FIGS. 25, 26, 27A–C and 28 illustrate several techniques used by the computer to orient the digital dentition model 500 properly. The computer first obtains a digital model of the dentition using one of the techniques described above (step 700). The computer then locates the model's z-axis 502, which in the depicted example extends from the base of the model toward the roof of the patient's mouth and is normal to the dentition's occlusal plane (step 702). The computer then locates the model's y-axis 504, which in the depicted example extends from an area lying within the dental arch toward the patient's front teeth (step 704). Using the right-hand rule, the computer then defines the model's x-axis 506 to extend from an area lying within the dental arch toward the teeth on the right side of the patient's mouth (step 706). The occlusal plane is a plane that is pierced by all of the cusps of the patient's teeth when the patient's mandibles interdigitate. Techniques for identifying the occlusal plane include receiving user input identifying the location of the plane and conducting a fully-automated analysis of the dentition model.

Figure 25:
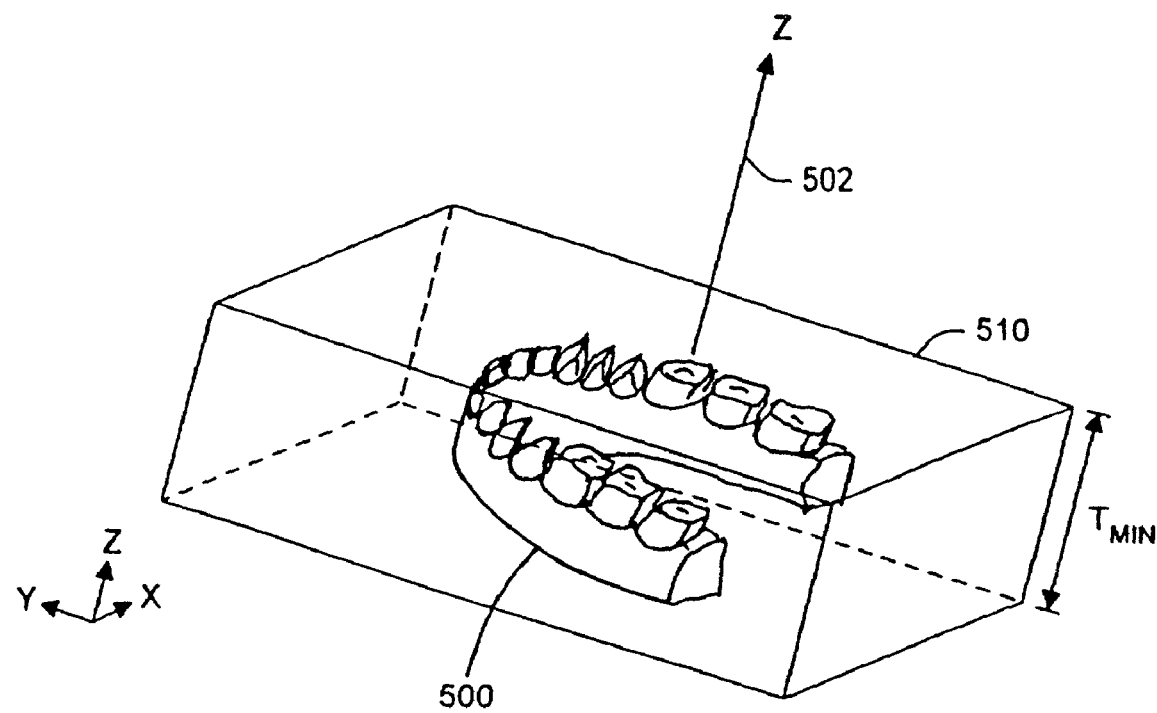
FIG. 25 shows a digital dentition model inside an Oriented Bounding Box (OBB).
Figure 26:
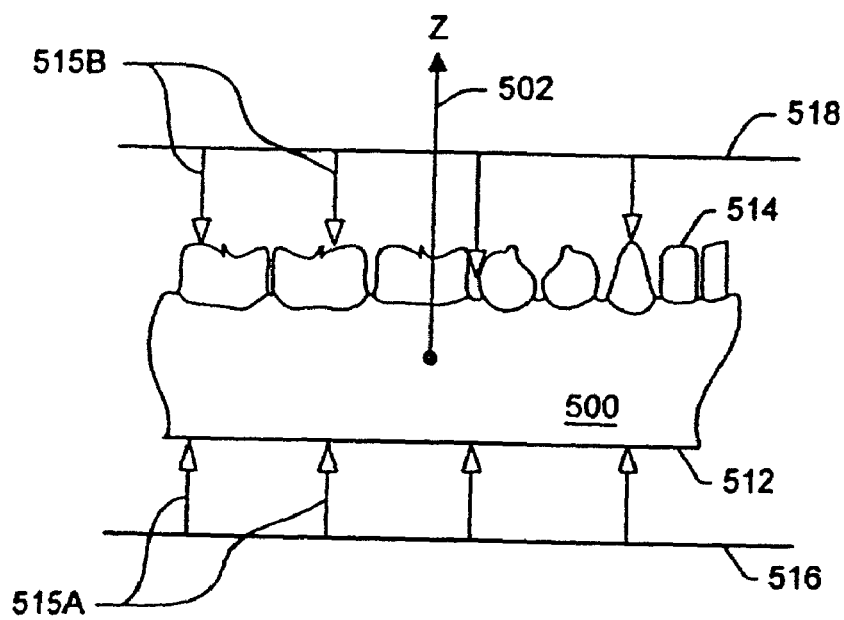
FIG. 26 illustrates a technique for properly orienting a digital dentition model along a z-axis.
Figure 27A:
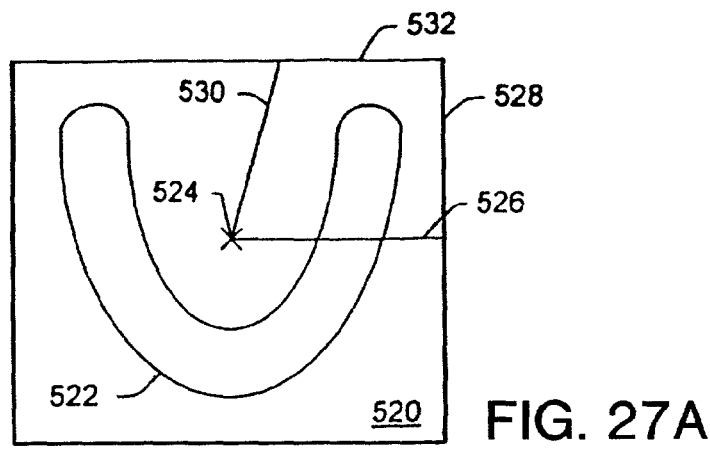
FIGS. 27A, 27B, and 27C illustrate a technique for properly orienting a digital dentition model along x- and y-axes.
Figure 27B:
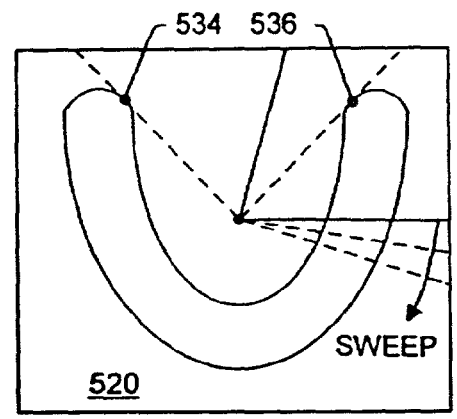
Figure 27C:
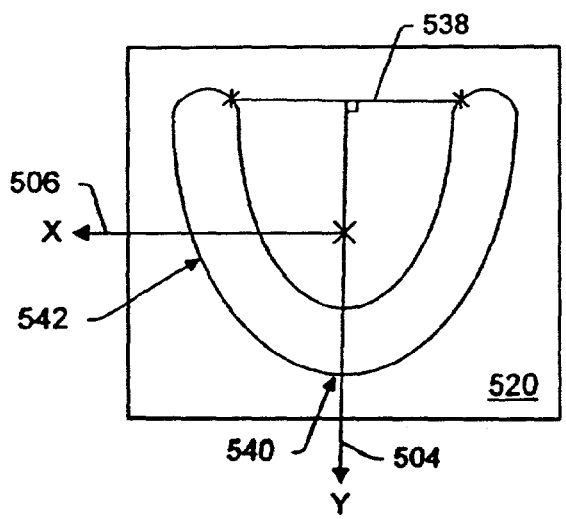
Figure 29:
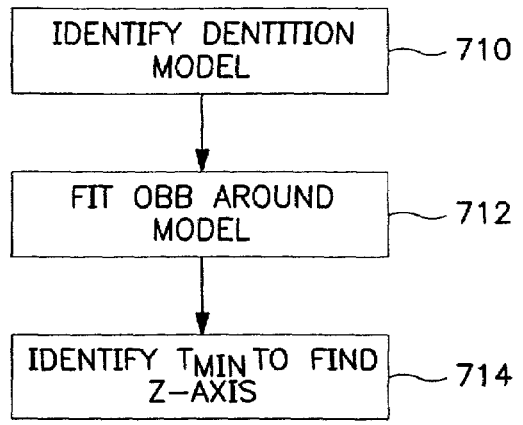
FIGS. 28, 29, 30 and 31 are flowcharts for the techniques of FIGS. 25, 26, and 27A-C.
Figure 28:
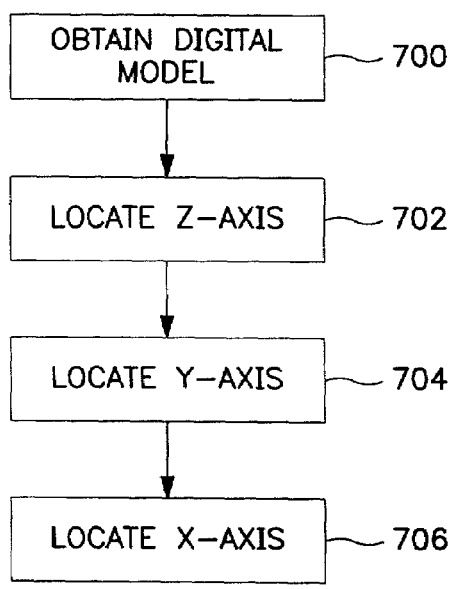

FIGS. 25, 26, and 29 show one technique for identifying the z-axis 502. The computer first identifies the dentition model 500 in the 3D data set (step 710). For 3D geometric data, identifying the dentition model is simply a matter of locating the geometric surfaces. For 3D volumetric data, identifying the dentition model involves distinguishing the lighter voxels, which represent the dentition model, from the darker voxels, which represent the background. The computer then fits an Oriented Bounding Box ("OBB") 510 around the dentition model 500 using a conventional OBB fitting technique (step 712). The dimension in which the OBB 510 has its smallest thickness TMIN is the dimension in which the z-axis 502 extends (step 714).

Figure 30:
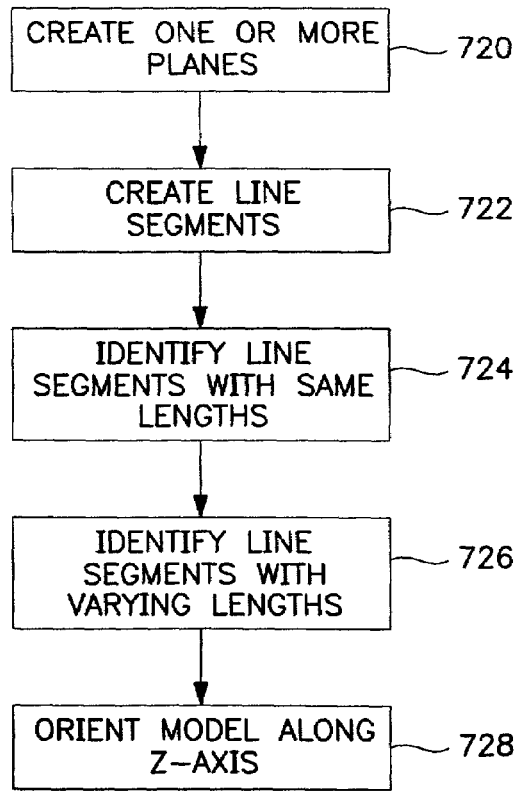
Figure 31:
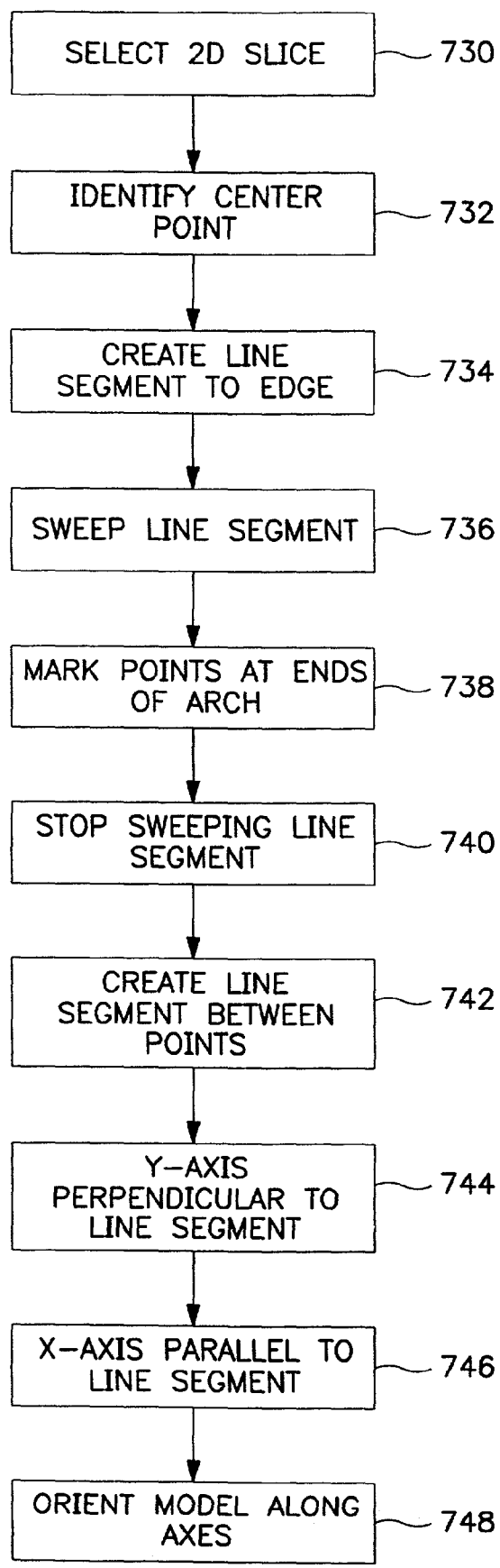

After determining the dimension in which the z-axis extends 502, the computer determines whether the dentition model is facing upward or downward, i.e., in which direction the positive z-axis extends. FIGS. 26 and 30 illustrate a technique for determining the direction of the positive z-axis. This technique relies on an observation that the bottom surface 512 of the dentition model is flat and the upper surface 514 follows the jagged contours of the patient's teeth. This technique also relies on an assumption that the model at this point includes only one of the patient's mandibles.

The computer first creates one or more planes 516, 518 that are normal to the z-axis 502 (step 720). The computer then creates line segments 515A, 515B between the planes 516, 518 and the surfaces 512, 514 of the model (step 722). The line segments 515A that touch the flat bottom surface 512 are all of approximately the same length (step 724). The line segments 5 15B that touch the jagged top surface 514 have varying lengths (step 726). The computer identifies the positive z-axis as extending from the bottom surface 512 toward the top surface 514 and orients the digital dentition model 500 accordingly (step 728).

FIGS. 27A, 27B, 27C, and 31 illustrate a technique for identifying the y-axis 504 and the x-axis 506 of the dentition model 500. The computer begins by selecting a 2D slice 520 of data that is normal to the z-axis and that contains a cross section 522 of the dentition model (step 730). This technique relies on an observation that the cross section 522 of the dentition model is arch shaped. The computer identifies a point 524 at or near the center of the 2D slice 520 (step 732). The computer then creates a line segment 526 (or 530) that extends from the selected point 524 to an edge 528 (or 532) of the slice 520 (step 734). The direction in which the line segment extends is arbitrary, so the line segment may or may not intersect the dental cross section. The depicted example shows two line segments 526, 530, one of which intersects the dental cross section 522, the other of which does not.

The computer then begins rotating, or sweeping, one of the line segments 526, 530 about the center point 524 (step 736). In general, the computer sweeps the line segment in small, discrete steps, usually on the order of five degrees of rotation. As it is swept, a line segment 526 that initially intersects the dental cross section 522 will eventually stop intersecting the cross section 522, and the computer marks the point 534 at which this occurs. As sweeping continues, the line segment 526 will eventually resume intersecting the cross section 522, and the computer marks the point 536 at which this occurs. Likewise, a line segment 530 that initially does not intersect the cross section 522 eventually will begin intersecting the cross section 522, and the computer marks the point 536 at which this occurs. The computer also marks the point 534 at which this line segment 530 stops intersecting the cross section 522 (step 738). The computer stops sweeping the line segments 526, 530 after marking both of the points 534, 536 (step 740).

The computer then creates a line segment 538 that extends between the two marked points 534, 536 (step 742). The y-axis 504 of the dentition model extends roughly normal to this line segment 538 through the front 540 of the dental arch (step 744). The x-axis 506 extends roughly parallel to this line segment 538 through the right side 542 of the dental arch (step 746). The computer uses this line segment 538 to orient the dentition model correctly along the x- and y-axes (step 748).

Segmenting the Digital Dentition Model Into Individual Component Models

Figure 1B:
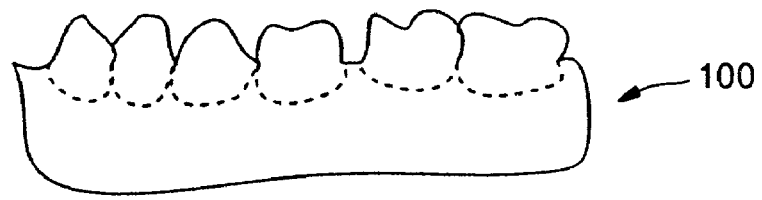
Figure 2:
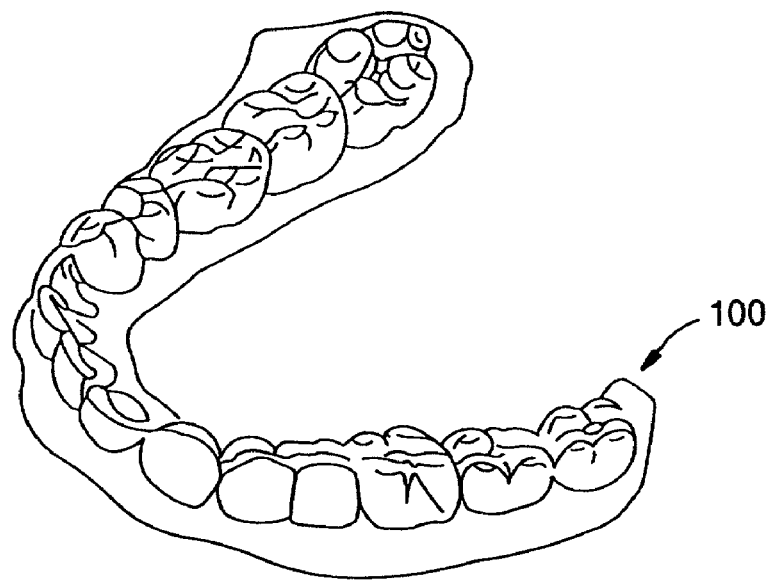

Some computer-implemented techniques for segmenting a 3D dentition model into models of individual dentition components require a substantial amount of human interaction with the computer. One such technique, which is shown in FIGS. 1A, 1B, and 2, provides a graphical user interface with a feature that imitates a conventional saw, allowing the user to identify components to be cut away from the dentition model 100. The graphical user interface provides a rendered 3D image 100 of the dentition model, either at one or more static views from predetermined positions, as shown in FIGS. 1A and 1B, or in a "full 3D" mode that allows the user to alter the viewing angle, as shown in FIG. 2. The saw tool is implemented as a set of mathematical control points 102, represented graphically on the rendered image 100, which define a 3D cutting surface 104 that intersects the volumetric or geometric dentition model. The computer subdivides the data elements in the dentition model by performing a surface intersection operation between the 3D cutting surface 104 and the dentition model. The user sets the locations of the mathematical control points, and thus the geometry and position of the 3D cutting surface, by manipulating the control points in the graphical display with an input device, such as a mouse. The computer provides a visual representation 104 of the cutting surface on the display to assist the user in fitting the surface around the individual component to be separated. Once the intersection operation is complete, the computer creates a model of the individual component using the newly segmented data elements.

Figure 3:
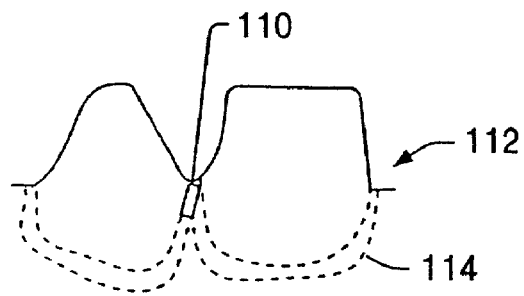
FIG. 3 is a partial view of a dentition model as displayed on a computer monitor and segmented with a human-operated eraser tool.

Another technique requiring substantial human interaction, shown in FIG. 3, is a graphical user interface with a tool that imitates a conventional eraser. The eraser tool allows the user to isolate an individual dentition component by removing portions of the dentition model that surround the individual component. The eraser tool is implemented as a 3D solid 110, typically having the shape of a rectangular prism, or a curved surface that matches the shape of a side surface of a tooth. The solid is made as small as possible, usually only a single voxel thick, to minimize degradation of the data set. As with the saw technique above, the graphical user interface presents the user with a rendered 3D image 112 of the dentition model at one or more predetermined static views or in a full 3D mode. The user identifies portions of the dentition model for removal by manipulating a graphical representation 110 of the 3D solid with an input device. In alternative embodiments, the computer either removes the identified portions of the dentition model as the user moves the eraser 112, or the computer waits until the user stops moving the eraser and provides an instruction to remove the identified portions. The computer updates the display in real time to show the path 114 of the eraser through the dentition model.

Figure 4:
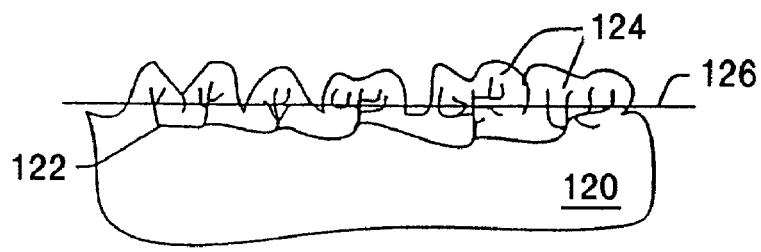
FIG. 4 is a view of a dentition model for which a feature skeleton has been identified.

Other computer-implemented segmentation techniques require little or no human interaction during the segmentation process. One such technique, which is illustrated in FIG. 4, involves the application of conventional "feature skeleton" analysis to a volumetric representation of the dentition model. This technique is particularly useful in identifying and modeling individual teeth. In general, a computer applying this technique identifies a core of voxels, that forms a skeleton 122 for the dentition 120. The skeleton 122 roughly resembles the network of biological nerves within patient's teeth. The computer then divides the skeleton 122 into branches 124, each containing voxels that lie entirely within one tooth. One technique for identifying the branches is by defining a plane 126 that cuts through the skeleton 122 roughly parallel to the occlusal plane of the patient's dentition ("horizontal plane"). Each branch 124 intersects the horizontal plane 126 at one or more points, or clusters, that are relatively distant from the clusters associated with the other branches. The computer forms the individual tooth models by linking other voxels to the appropriate branches 124 of the skeleton.

Figure 5:
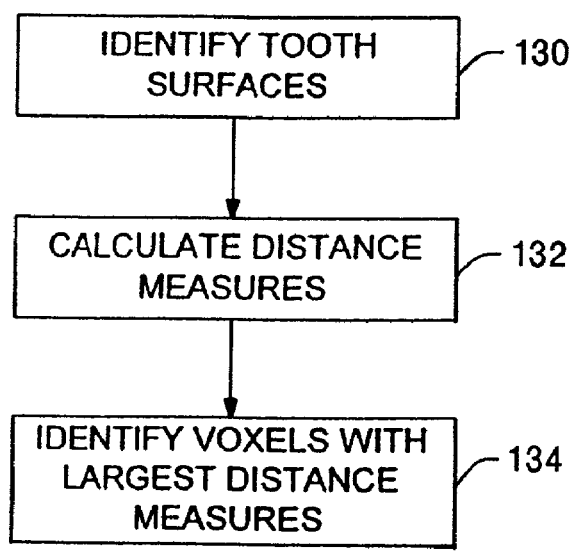
FIGS. 5 and 6 are flowcharts for a feature skeleton analysis technique used in segmenting a dentition model.

FIG. 5 describes a particular technique for forming a skeleton in the dentition model. The computer first identifies the voxels in the dentition model that represent the tooth surfaces (step 130). For a voxel representation that is created from a physical model embedded in a sharply contrasting material, identifying the tooth surfaces is as simple as identifying the voxels at which sharp changes in image value occur, as described in U.S. patent application Ser. No. 09/169,276. The computer then calculates, for each voxel in the model, a distance measure indicating the physical distance between the voxel and the nearest tooth surface (step 132). The computer identifies the voxels with the largest distance measures and labels each of these voxels as forming a portion of the skeleton (step 134). Feature skeleton analysis techniques are described in more detail in the following publications: (1) Gagvani and Silver, "Parameter Controlled Skeletons for 3D Visualization," Proceedings of the IEEE Visualization Conference (1997); (2) Bertrand, "A Parallel Thinning Algorithm for Medial Surfaces," Pattern Recognition Letters, v. 16, pp. 979–986 (1995); (3) Mukherjee, Chatterji, and Das, "Thinning of 3-D Images Using the Safe Point Thinning Algorithm (SPTA)," Pattern Recognition Letters, v. 10, pp. 167–173 (1989); (4) Niblack, Gibbons, and Capson, "Generating Skeletons and Centerlines from the Distance Transform," CVGIP: Graphical Models and Image Processing, v. 54, n. 5, pp. 420–437 (1992).

Figure 6:
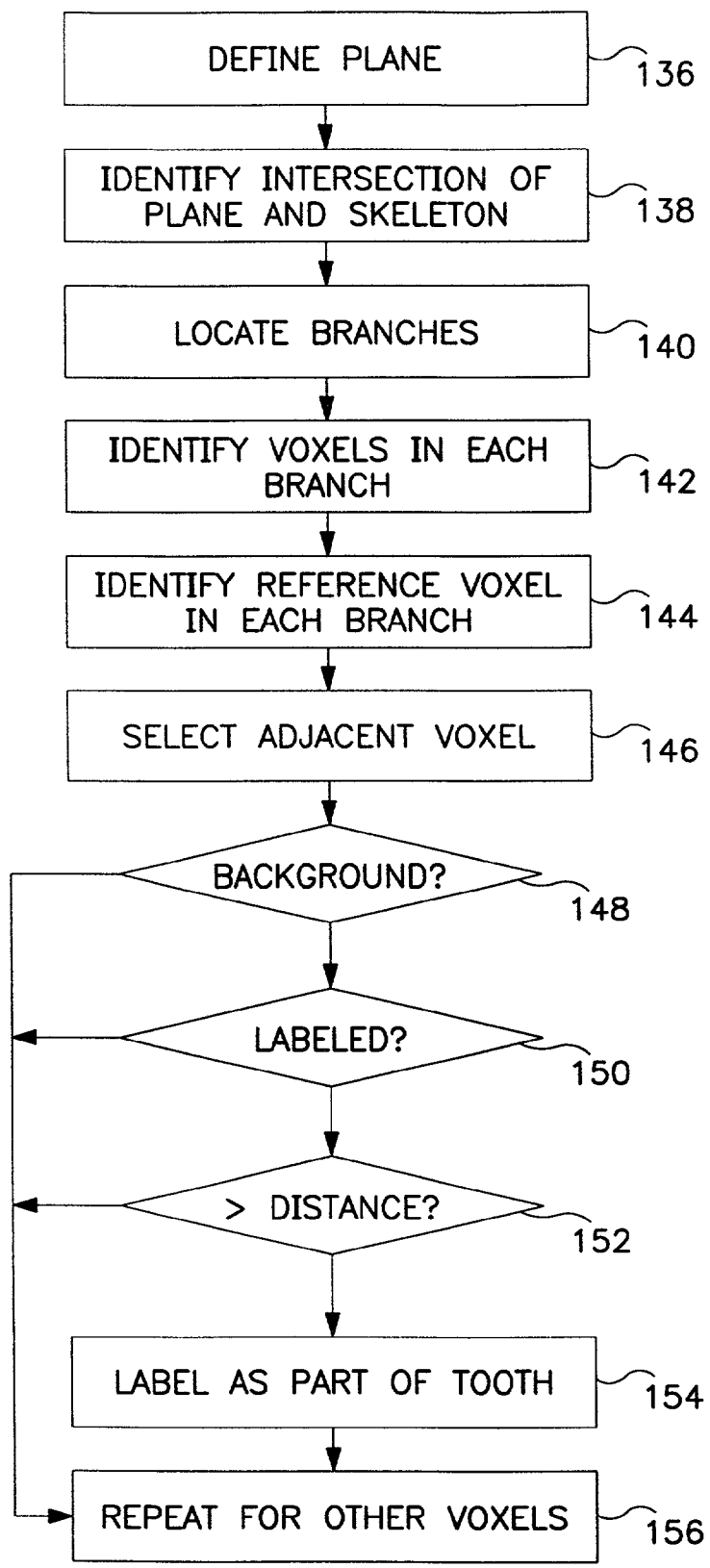

Once a skeleton has been formed, the computer uses the skeleton to divide the dentition model into 3D models of the individual teeth. FIG. 6 shows one technique for doing so. The computer first identifies those portions of the skeleton that are associated with each individual tooth. To do so, the computer defines a plane that is roughly parallel to the dentition's occlusal surface and that intersects the skeleton near its base (step 136). The computer then identifies points at which the plane and the skeleton intersect by identifying each voxel that lies on both the skeleton and the plane (step 138). In general, a single tooth includes all of the voxels that lie in a particular branch of the skeleton; and because the plane intersects the skeleton near its base, voxels that lie together in a branch of the skeleton usually cluster together on the intersecting plane. The computer is able to locate the branches by identifying voxels on the skeleton that lie within a particular distance of each other on the intersecting plane (step 140). The computer then identifies and labels all voxels on the skeleton that belong to each branch (step 142).

Once the branches are identified, the computer links other voxels in the model to the branches. The computer begins by identifying a reference voxel in each branch of the skeleton (step 144). For each reference voxel, the computer selects an adjacent voxel that does not lie on the skeleton (step 146). The computer then processes the selected voxel, determining whether the voxel lies outside of the dentition, i.e., whether the associated image value is above or below a particular threshold value (step 148); determining whether the voxel already is labeled as belonging to another tooth (step 150); and determining whether the voxel's distance measure is greater than the distance measure of the reference voxel (step 152). If none of these conditions is true, the computer labels the selected voxel as belonging to the same tooth as the reference voxel (step 154). The computer then repeats this test for all other voxels adjacent to the reference voxel (step 156). Upon testing all adjacent voxels, the computer selects one of the adjacent voxels as a new reference point, provided that the adjacent voxel is labeled as belonging to the same tooth, and then repeats the test above for each untested voxel that is adjacent to the new reference point. This process continues until all voxels in the dentition have been tested.

Figure 7A:
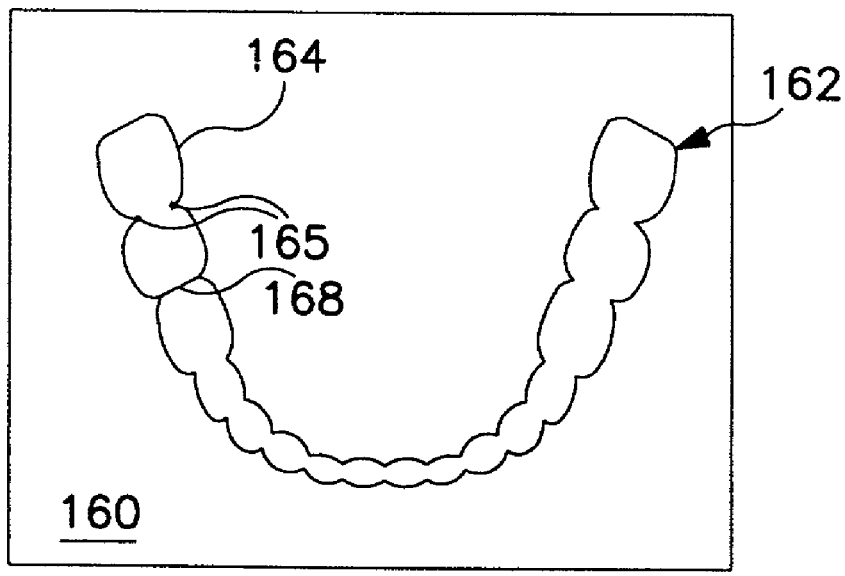
FIG. 7A is a horizontal 2D cross-sectional view of a dentition model.
Figure 7B:
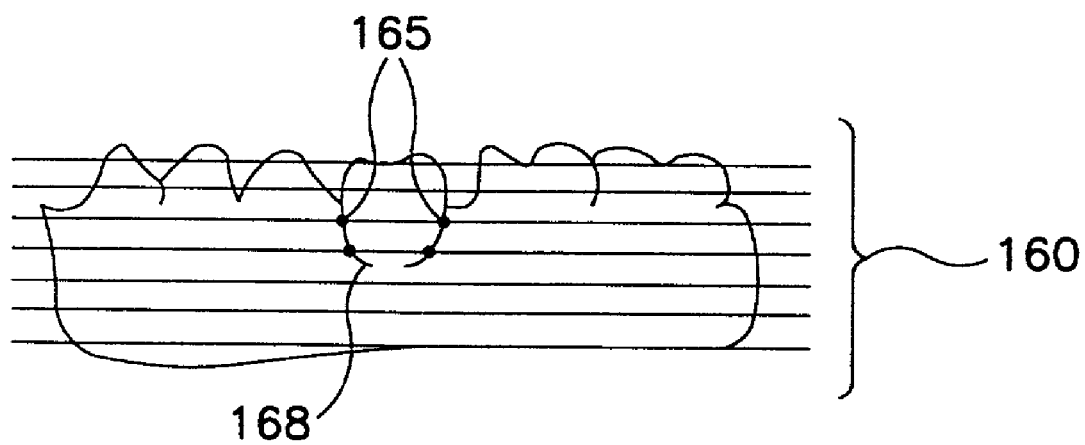
FIG. 7B is a side view of a dentition model intersected by several 2D planes.

FIGS. 7A and 7B illustrate another technique for identifying and segmenting individual teeth in the dentition model. This technique, called "2D slice analysis," involves dividing the voxel representation of the dentition model into a series of parallel 2D planes 160, or slices, that are each one voxel thick and that are roughly parallel to the dentition's occlusal plane, which is roughly normal to the model's z-axis. Each of the 2D slices 160 includes a 2D cross section 162 of the dentition, the surface 164 of which represents the lingual and buccal surfaces of the patient's teeth and/or gums. The computer inspects the cross section 162 in each 2D slice 160 to identify voxels that approximate the locations of the interproximal margins 166 between the teeth. These voxels lie at the tips of cusps 165 in the 2D cross-sectional surface 164. The computer then uses the identified voxels to create 3D surfaces 168 intersecting the dentition model at these locations. The computer segments the dentition model along these intersecting surfaces 168 to create individual tooth models.

Figure 8:
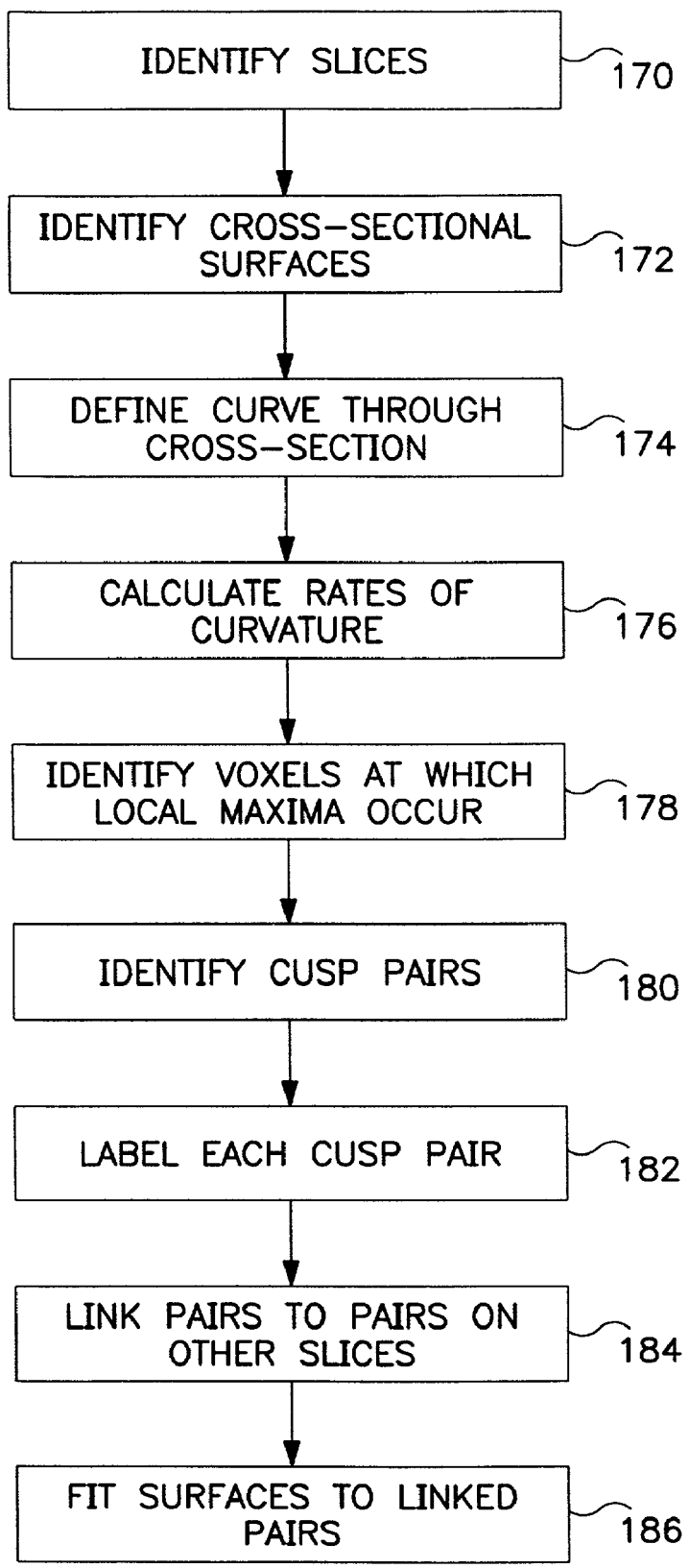
FIG. 8 is a flowchart for a 2D slice analysis technique used in segmenting a dentition model.

FIG. 8 describes a particular implementation of the 2D slice analysis technique. The computer begins by identifying the voxels that form each of the 2D slices (step 170). The computer then identifies, for each 2D slice, the voxels that represent the buccal and lingual surfaces of the patient's teeth and gums (step 172) and defines a curve that includes all of these voxels (step 174). This curve represents the surface 164 of the 2D cross section 162.

The computer then calculates the rate of curvature (i.e., the derivative of the radius of curvature) at each voxel on the 2D cross-sectional surface 164 (step 176) and identifies all of the voxels at which local maxima in the rate of curvature occur (step 178). Each voxel at which a local maximum occurs represents a "cusp" in the 2D cross-sectional surface 164 and roughly coincides with an interproximal margin between teeth. In each 2D slice, the computer identifies pairs of these cusp voxels that correspond to the same interproximal margin (step 180), and the computer labels each pair to identify the interproximal margin with which it is associated (step 182). The computer then identifies the voxel pairs on all of the 2D slices that represent the same interproximal margins (step 184). For each interproximal margin, the computer fits a 3D surface 168 approximating the geometry of the interproximal margin among the associated voxel pairs (step 186).

Figure 9:
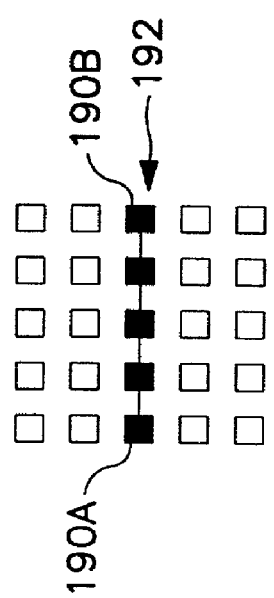

FIG. 9 illustrates one technique for creating the 3D surfaces that approximate the interproximal margins. For each pair of cusp voxels 190a–b in a 2D slice that are associated with a particular interproximal region, the computer creates a line segment 192 bounded by these cusp voxels 190a–b. The computer changes the colors of the voxels in the line segment, including the cusp voxels 190a–b that bound the segment, to contrast with the other voxels in the 2D slice. The computer creates line segments in this manner in each successive 2D slice, forming 3D surfaces that represent the interproximal regions. All of the voxels that lie between adjacent ones of these 3D surfaces represent an individual tooth.

Figure 10A:
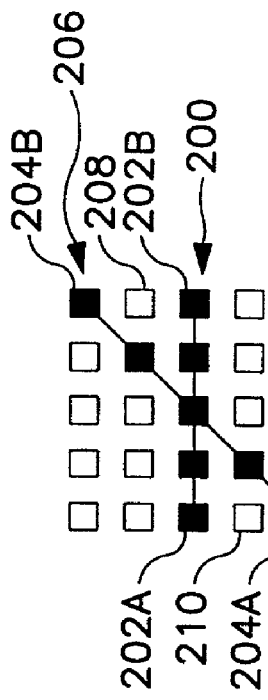
FIGS. 9 and 10A through 10C each shows a group of voxels in a 2D slice of a dentition model.
Figure 10C:
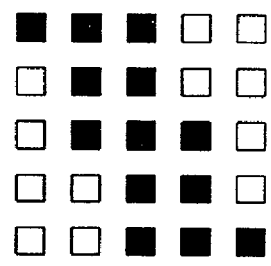
Figure 10B:
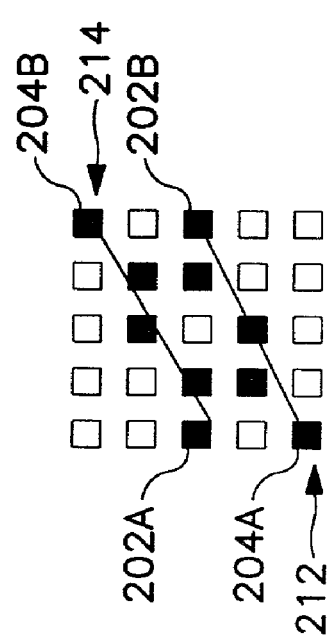

FIGS. 10A through 10C illustrate a refinement of the technique shown in FIG. 9. The refined technique involves the projection of a line segment 200 from one slice onto a line segment 206 on the next successive slice to form, for the associated interproximal margin, a 2D area bounded by the cusp voxels 202a–b, 204a–b of the line segments 200, 206. If the line segments 200, 206 are oriented such that any voxel on one segment 200 is not adjacent to a voxel on the other segment 206, as shown in FIG. 10A, then the resulting 3D surface is discontinuous, leaving unwanted "islands" of white voxels 208, 210.

The computer eliminates these discontinuities by creating two new line segments 212, 214, each of which is bounded by one cusp voxel 202a–b, 204a–b from each original line segment 200, 206, as shown in FIG. 10B. The computer then eliminates the islands between the new line segments 212, 214 by changing the colors of all voxels between the new line segments 212, 214, as shown in FIG. 10C.

Automated segmentation is enhanced through a technique known as "seed cusp detection." The term "seed cusp" refers to a location at which an interproximal margin between adjacent teeth meets the patient's gum tissue. In a volumetric representation of the patient's dentition, a seed cusp for a particular interproximal margin is found at the cusp voxel that lies closest to the gum line. By applying the seed cusp detection technique to the 2D slice analysis, the computer is able to identify all of the seed cusp voxels in the 3D model automatically.

Figure 11:
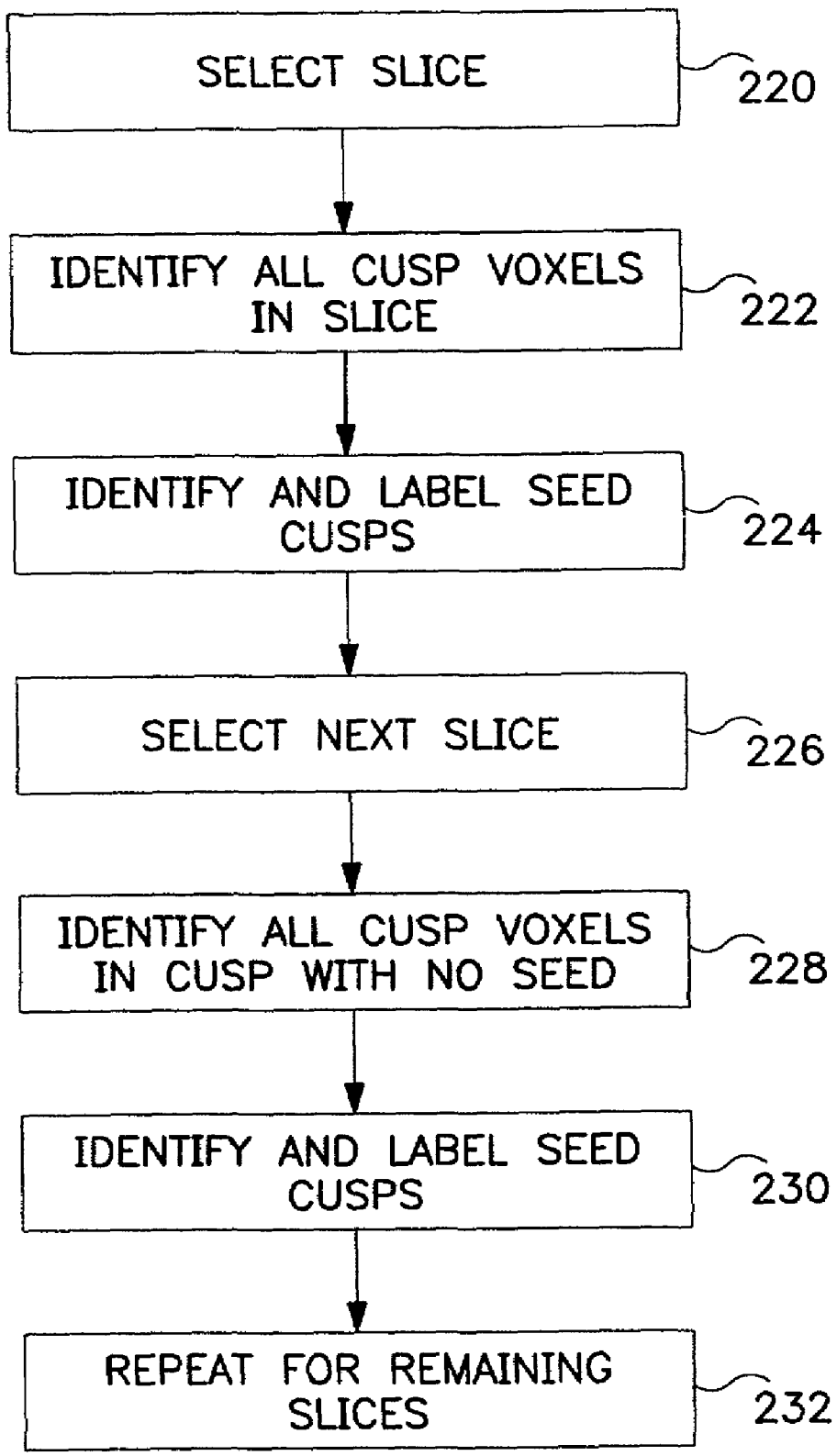
FIG. 11 is a flowchart for an automatic cusp detection technique used in segmenting a dentition model.

FIG. 11 shows a particular implementation of the seed cusp detection technique, in which the computer detects the seed cusps by identifying each 2D slice in which the rate of curvature of a cusp first falls below a predetermined threshold value. The computer begins by selecting a 2D slice that intersects all of the teeth in the arch (step 220). The computer attempts to select a slice that is near the gingival regions but that does not include any voxels representing gingival tissue. The computer then identifies all of the cusp voxels in the 2D slice (step 222). If the rate of curvature of the 2D cross section at any of the cusp voxels is less than a predetermined threshold value, the computer labels that voxel as a seed cusp (step 224). The computer then selects the next 2D slice, which is one voxel layer closer to the gingival region (step 226), and identifies all of the cusp voxels that are not associated with a cusp for which the computer has already identified a seed cusp (step 228). If the rate of curvature of the 2D cross section is less than the predetermined threshold value at any of these cusp voxels, the computer labels the voxel as a seed cusp (step 230) and proceeds to the next 2D slice. The computer continues in this manner until a seed cusp voxel has been identified for each cusp associated with an interproximal margin (step 232).

Figure 32:
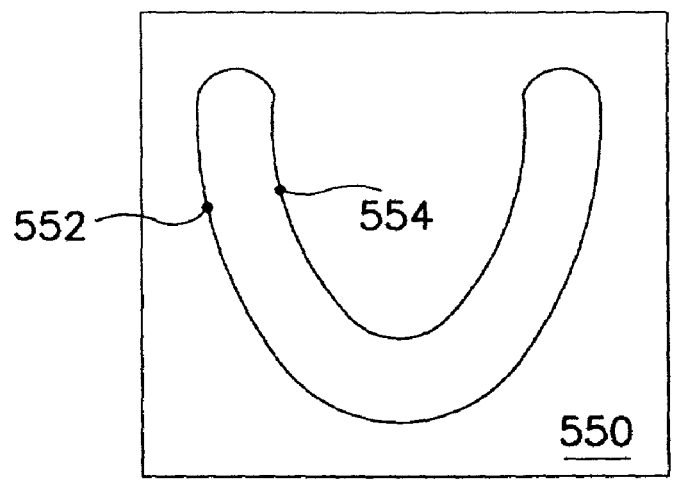
FIGS. 32 and 33 illustrate a human-assisted technique for identifying interproximal margins between teeth.
Figure 33:
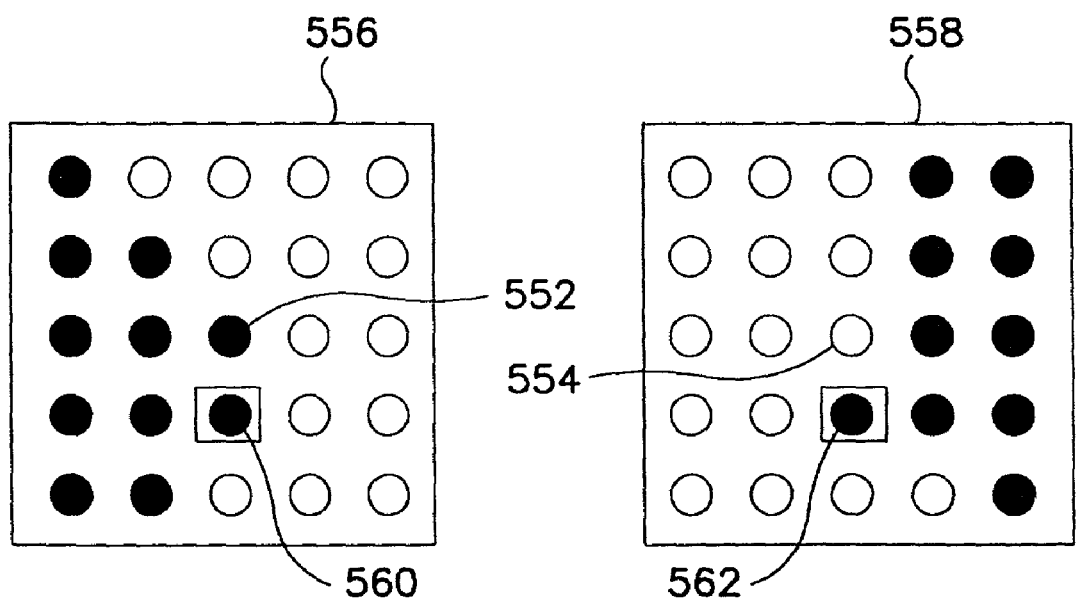
Figure 34:
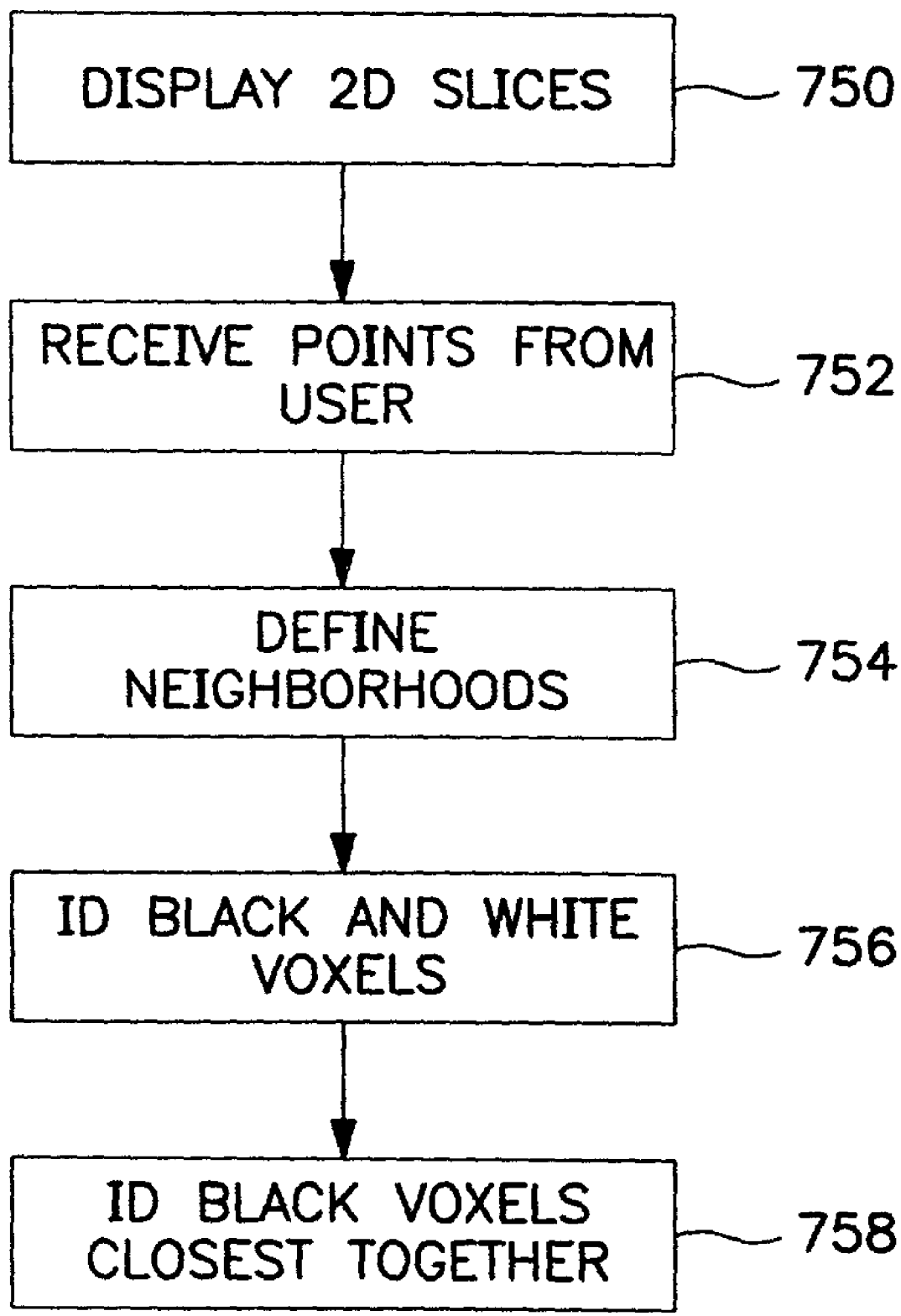
FIG. 34 is a flowchart for the technique of FIGS. 32 and 33.
Figure 35A:
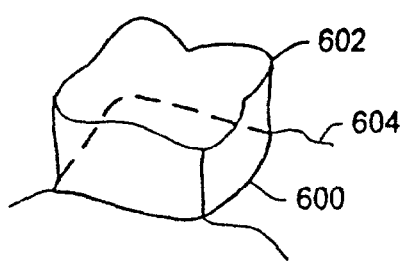
FIGS. 35A through 35F illustrate a technique for segmenting a digital dentition model into models of individual teeth and gum tissue.
Figure 35B:
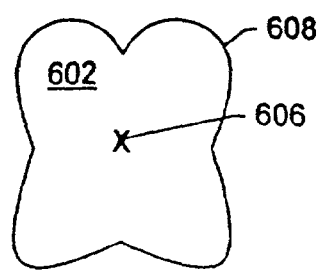
Figure 35C:
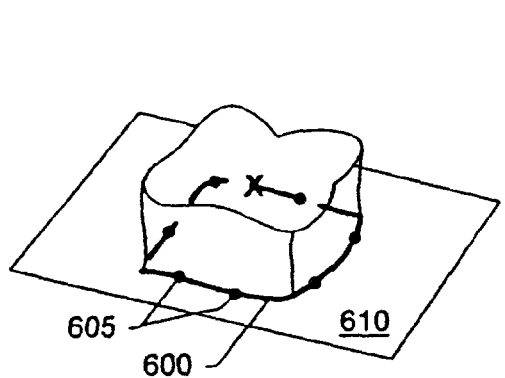
Figure 35D:
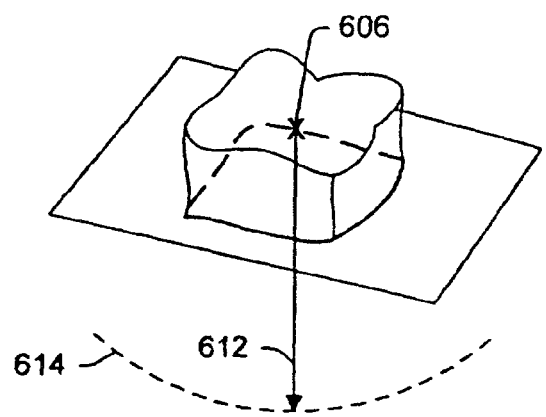
Figure 35E:
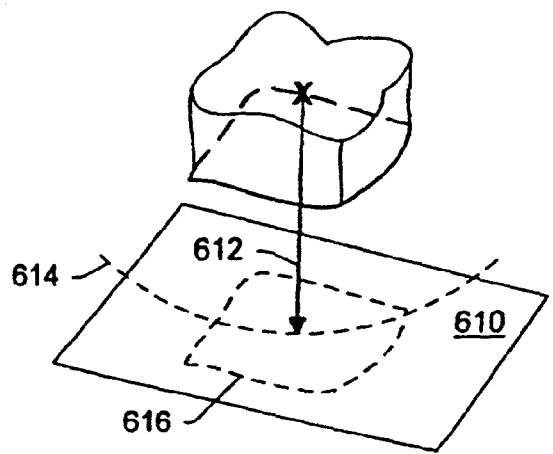
Figure 35F:
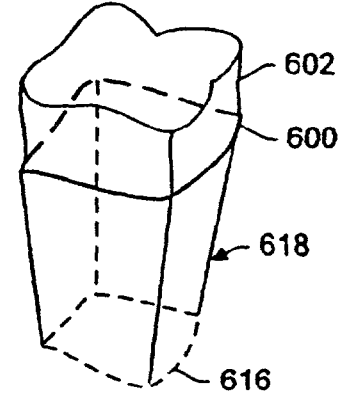
Figure 36:
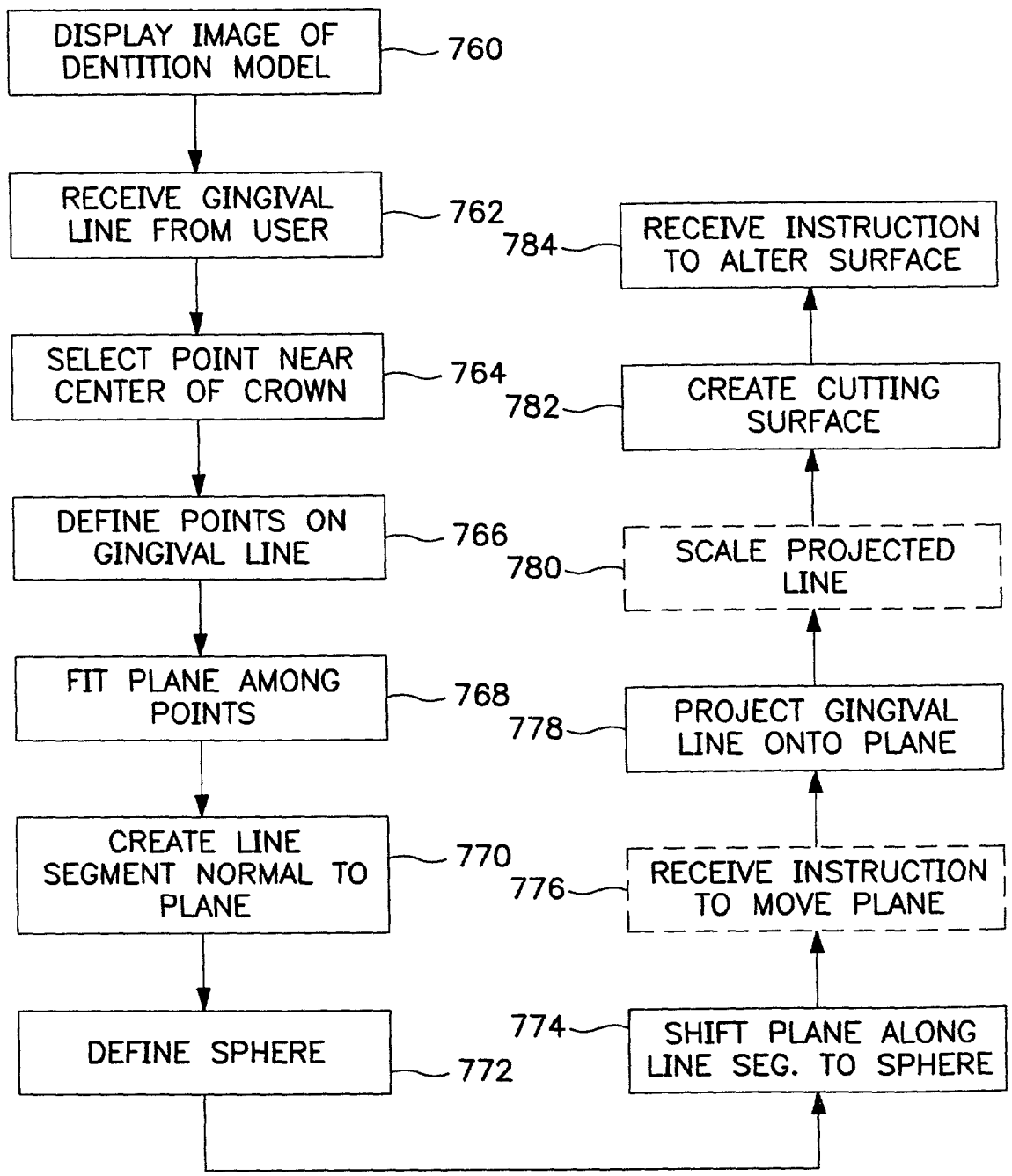
FIG. 36 is a flowchart for the technique of FIGS. 35A through 35F.

FIGS. 32, 33, and 34 illustrate a human-assisted technique, known as "neighborhood-filtered seed cusp detection," for detecting seed cusps in the digital dentition model. This technique allows a human operator to scroll through 2D image slices on a video display and identify the locations of the seed cusps for each of the interproximal margins. The computer displays the 2D slices (step 750), and the operator searches the 2D slices to determine, for each adjacent pair of teeth, which slice 550 most likely contains the seed cusps for the corresponding interproximal margin. Using an input device such as a mouse or an electronic pen, the user marks the points 552, 554 in the slice 550 that appear to represent the seed cusps (step 752). With this human guidance, the computer automatically identifies two voxels in the slice as the seed cusps.

The points 552, 554 identified by the human operator may or may not be the actual seed cusps 560, 562, but these points 552, 554 lie very close to the actual seed cusps 560, 562. As a result, the computer confines its search for the actual seed cusps 560, 562 to the voxel neighborhoods 556, 558 immediately surrounding the points 552, 554 selected by the human operator. The computer defines each of the neighborhoods 556, 558 to contain a particular number of voxels, e.g., twenty-five arranged in a 5×5 square, as shown here (step 754). The computer then tests the image values for all of the voxels in the neighborhoods 556, 558 to identify those associated with the background image and those associated with the dentition (step 756). In this example, voxels in the background are black and voxels in the dentition are white. The computer identifies the actual seed cusps 560, 562 by locating the pair of black voxels, one from each of the neighborhoods 556, 558, that lie closest together (step 758). In the depicted example, each of the actual seed cusps 560, 562 lies next to one of the points 552, 554 selected by the human operator.

Figure 12:
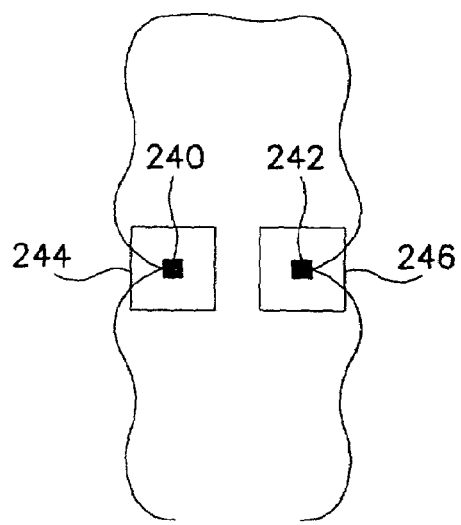
FIG. 12 is a horizontal 2D cross section of a dentition model illustrating a neighborhood filtered automatic cusp detection technique used in segmenting the dentition model.
Figure 13:
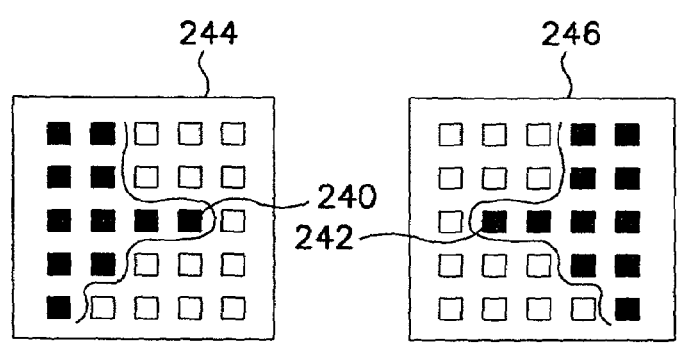
FIG. 13 shows two groups of voxels in a 2D slice of a dentition model illustrating the neighborhood filtered automatic cusp detection technique.
Figure 14:
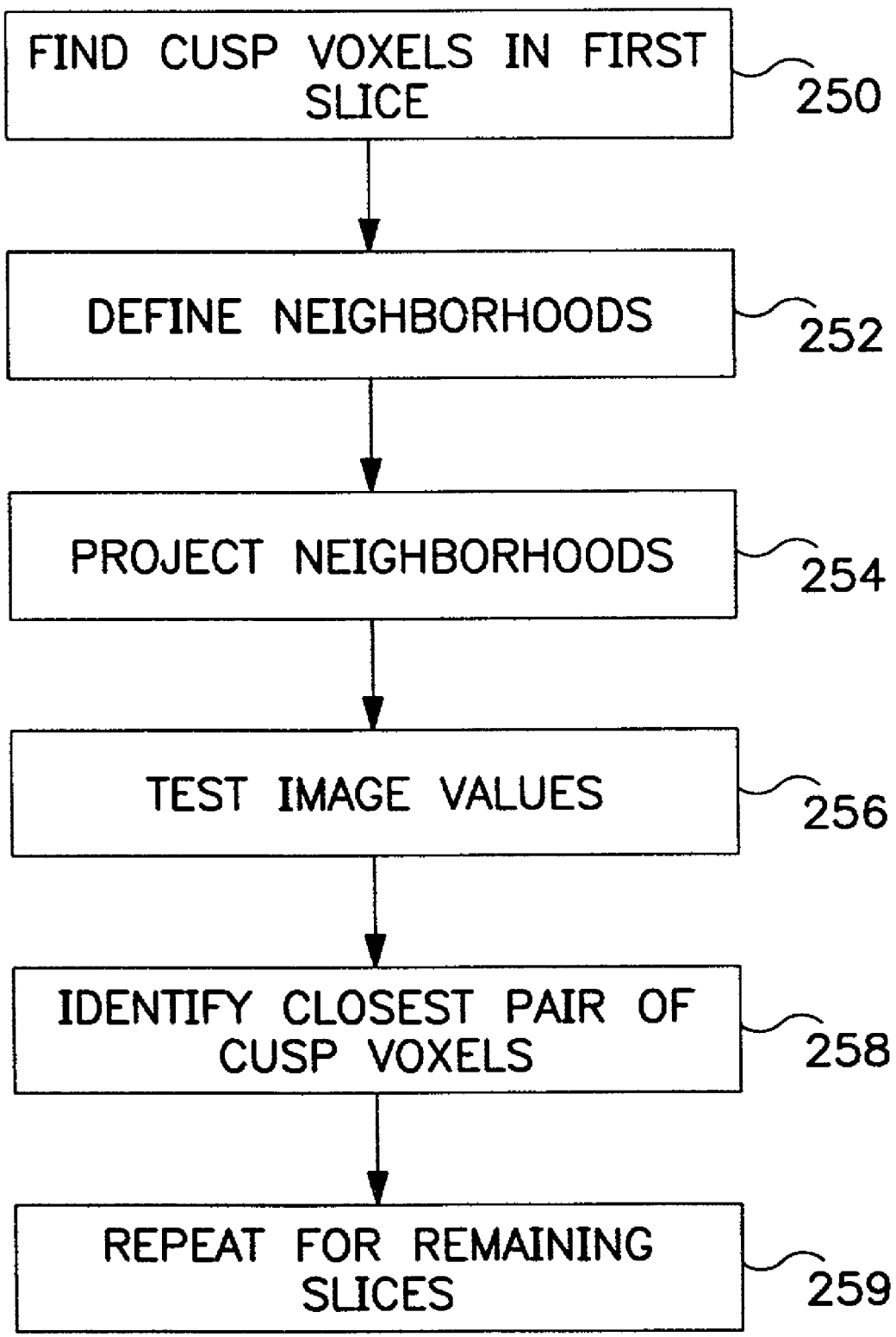
FIG. 14 is a flowchart for the neighborhood filtered automatic cusp detection technique.

FIGS. 12, 13, and 14 illustrate a technique, known as "neighborhood-filtered cusp detection," by which the computer focuses its search for cusps on one 2D slice to neighborhoods 244, 246 of voxels defined by a pair of previously detected cusp voxels 240, 242 on another 2D slice. This technique is similar to the neighborhood-filtered seed cusp detection technique described above.

Upon detecting a pair of cusp voxels 240, 242 in a 2D slice at level N (step 250), the computer defines one or more neighborhoods 244, 246 that include a predetermined number of voxels surrounding the pair (step 252). The computer then projects the neighborhoods onto the next 2D slice at level N+1 by identifying the voxels on the next slice that are immediately adjacent the voxels in the neighborhoods on the original slice (step 254). The neighborhoods are made large enough to ensure that they include the cusp voxels on the N+1 slice. In the example of FIG. 13, each cusp voxel 240, 242 lies at the center of a neighborhood 244, 246 of twenty-five voxels arranged in a 5×5 square.

In searching for the cusp voxels on the N+1 slice, the computer tests the image values for all voxels in the projected neighborhoods to identify those associated with the background image and those associated with the dentition (step 256). In the illustrated example, voxels in the background are black and voxels in the dentition are white. The computer identifies the cusp voxels on the N+1 slice by locating the pair of black voxels in the two neighborhoods that lie closest together (step 258). The computer then repeats this process for all remaining slices (step 259).

Figure 15:
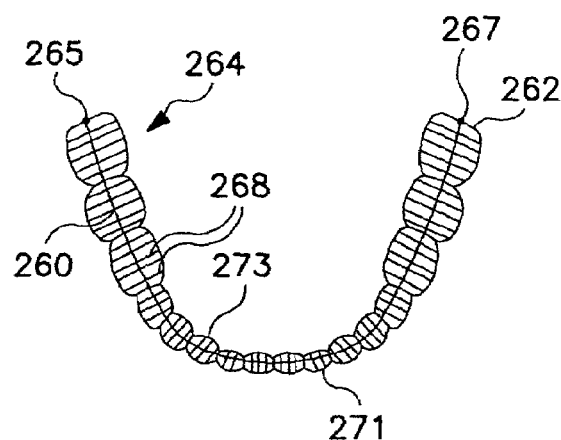
FIG. 15 is a horizontal 2D cross section of a dentition model illustrating an arch curve fitting technique used in segmenting the dentition model.
Figure 16:
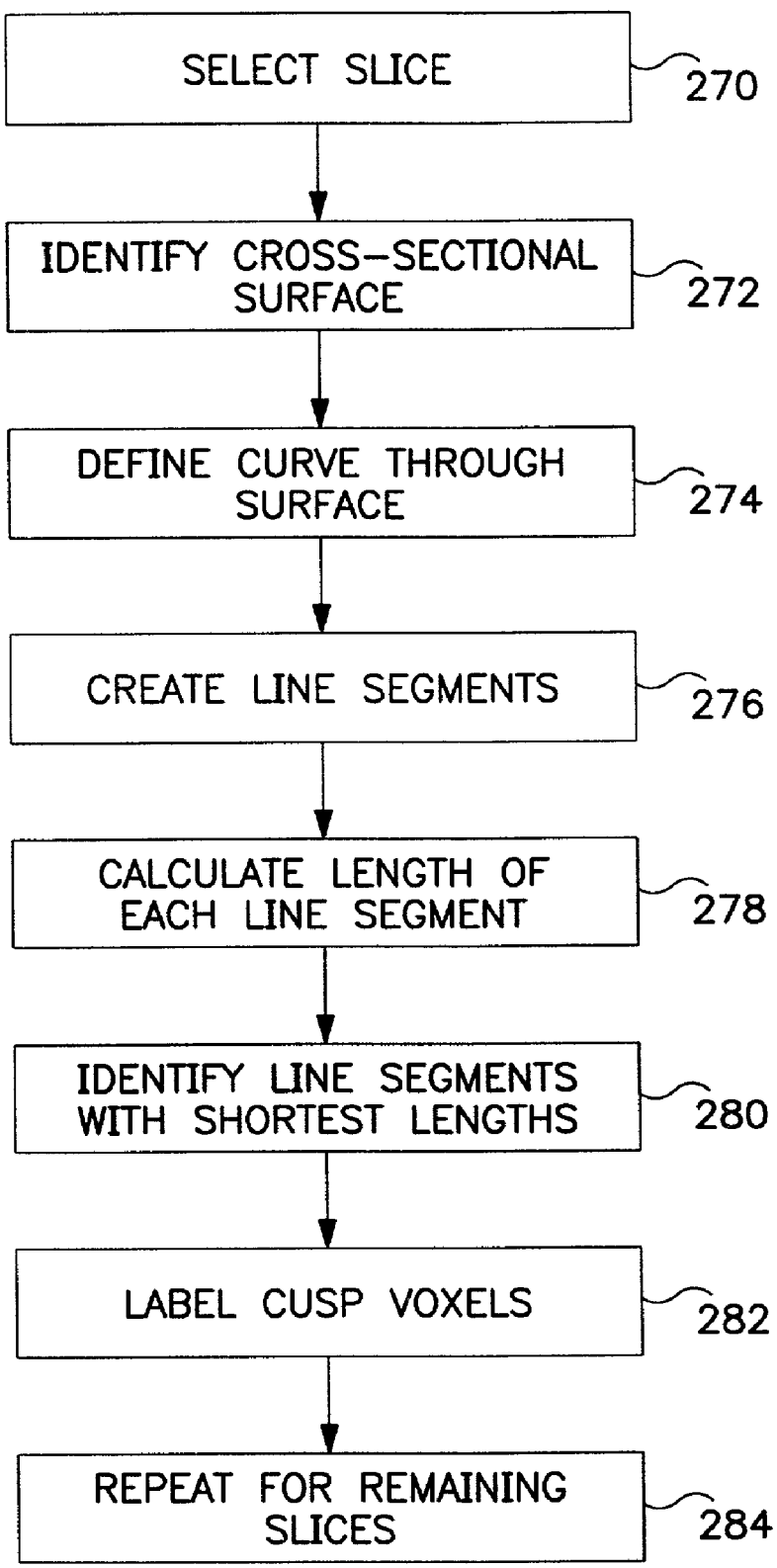
FIG. 16 is a flowchart for the arch curve fitting technique.

FIGS. 15 and 16 illustrate another technique, known as "arch curve fitting," for identifying interproximal margins between teeth in the dentition. The arch curve fitting technique, which also applies to 2D cross-sectional slices of the dentition, involves the creation of a curve 260 that fits among the voxels on the 2D cross-sectional surface 262 of the dentition arch 264. A series of closely spaced line segments 268, each bounded by the cross-sectional surface 268, are formed along the curve 260, roughly perpendicular to the curve 260, throughout the 2D cross section 264. In general, the shortest of these line segments 268 lie on or near the interproximal margins; thus computer identifies the cusps that define the interproximal margins by determining the relative lengths of the line segments 268.

When applying the arch curve fitting technique, the computer begins by selecting a 2D slice (step 270) and identifying the voxels associated with the surface 262 of the cross-sectional arch 264 (step 272). The computer then defines a curve 260 that fits among the voxels on the surface 262 of the arch (step 274). The computer creates the curve using any of a variety of techniques, a few of which are discussed below. The computer then creates a series of line segments that are roughly perpendicular to the curve and are bounded by the cross-sectional surface 262 (step 276). The line segments are approximately evenly spaced with a spacing distance that depends upon the required resolution and the acceptable computing time. Greater resolution leads to more line segments and thus greater computing time. In general, a spacing on the order of 0.4 mm is sufficient in the initial pass of the arch curve fitting technique.

The computer calculates the length of each line segment (step 278) and then identifies those line segments that form local minima in length (step 280). These line segments roughly approximate the locations of the interproximal boundaries, and the computer labels the voxels that bound these segments as cusp voxels (step 282). The computer repeats this process for each of the 2D slices (step 284) and then uses the cusp voxels to define 3D cutting surfaces that approximate the interproximal margins.

In some implementations, the computer refines the arch cusp determination by creating several additional sets of line segments, each centered around the arch cusps identified on the first pass. The line segments are spaced more narrowly on this pass to provide greater resolution in identifying the actual positions of the arch cusps.

The computer uses any of a variety of curve fitting techniques to create the curve through the arch. One technique involves the creation of a catenary curve with endpoints lying at the two ends 265, 267 (FIG. 15) of the arch. The catenary curve is defined by the equation $y = a + b \cdot \cosh(cx)$, and the computer fits the curve to the arch by selecting appropriate values for the constants a, b, and c. Another technique involves the creation of two curves, one fitted among voxels lying on the front surface 271 of the arch, and the other fitted among voxels on the rear surface 273. A third curve, which guides the placement of the line segments above, passes through the middle of the area lying between the first two curves.

Figure 18:
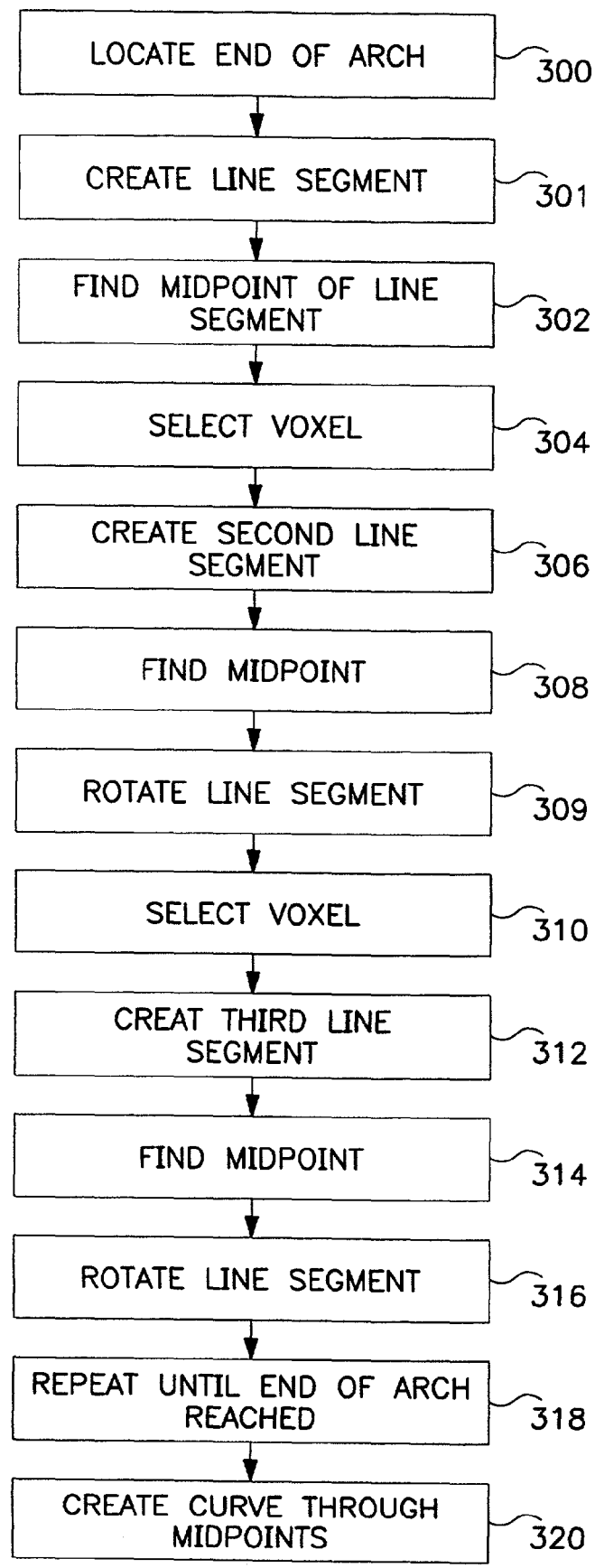
FIG. 18 is a flowchart for the curve creation technique.

FIGS. 17 and 18 illustrate another technique for constructing a curve through the arch. This technique involves the creation of a series of initial line segments through the arch 264 and the subsequent formation of a curve 290 fitted among the midpoints of these line segments This curve 290 serves as the arch curve in the arch curve fitting technique described above.

In applying this technique, the computer first locates an end 265 of the arch (step 300) and creates a line segment 291 that passes through the arch 264 near this end 265 (step 301). The line segment 291 is bounded by voxels 292*a–b* lying on the surface of the arch. The computer then determines the midpoint 293 of the line segment 291 (step 302), selects a voxel 294 located particular distance from the midpoint 293 (step 304), and creates a second line segment 295 that is parallel to the initial line segment 291 and that includes the selected voxel 294 (step 306). The computer then calculates the midpoint 296 of the second segment 295 (step 308) and rotates the second segment 295 to the orientation 295' that gives the segment its minimum possible length (step 309). In some cases, the computer limits the second segment 295 to a predetermined amount of rotation (e.g., ±10°).

The computer then selects a voxel 297 located a particular distance from the midpoint 296 of the second segment 295 (step 310) and creates a third line segment 298 that is parallel to the second line segment 295 and that includes the selected voxel 297 (step 312). The computer calculates the midpoint 299 of the third segment 298 (step 314) and rotates the segment 298 to the orientation 298'that gives the segment its shortest possible length (step 316). The computer continues adding line segments in this manner until the other end of the cross-sectional arch is reached (step 318). The computer then creates a curve that fits among the midpoints of the line segments (step 320) and uses this curve in applying the arch fitting technique described above.

Figure 20:
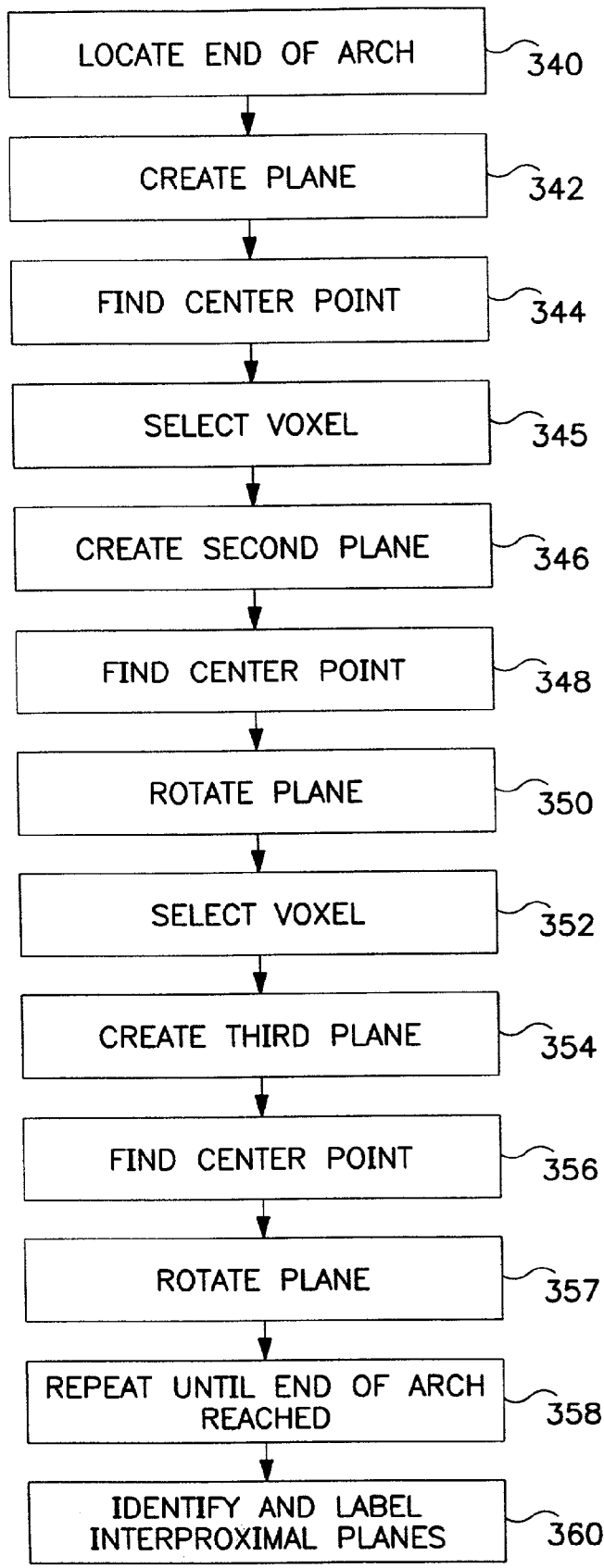
FIGS. 20 and 21 are flowcharts of the technique illustrated in FIGS. 19A and 19B.

FIGS. 19A, 19B and 20 illustrate an alternative technique for creating 3D surfaces that approximate the geometries and locations of the interproximal margins in the patient's dentition. This technique involves the creation of 2D planes that intersect the 3D dentition model at locations that approximate the interproximal margins. In general, the computer defines a series of planes, beginning with an initial plane 330 at one end 331 of the arch 332, that are roughly perpendicular to the occlusal plane of the dentition model ("vertical" planes). Each plane intersects the dentition model to form a 2D cross section 334. If the planes are spaced sufficiently close to each other, the planes with the smallest cross-sectional areas approximate the locations of the interproximal margins in the dentition. The computer locates the interproximal regions more precisely by rotating each plane about two orthogonal axes 336, 338 until the plane reaches the orientation that yields the smallest possible cross-sectional area.

In one implementation of this technique, the computer first identifies one end of the arch in the dentition model (step 340). The computer then creates a vertical plane 330 through the arch near this end (step 342) and identifies the center point 331 of the plane 330 (step 344). The computer then selects a voxel located a predetermined distance from the center point (step 345) and creates a second plane 333 that is parallel to the initial plane and that includes the selected voxel (step 346). The computer calculates the midpoint of the second plane (step 348) and rotates the second plane about two orthogonal axes that intersect at the midpoint (step 350). The computer stops rotating the plane upon finding the orientation that yields the minimum cross-sectional area. In some cases, the computer limits the plane to a predetermined amount of rotation (e.g., ±10 about each axis). The computer then selects a voxel located a particular distance from the midpoint of the second plane (step 352) and creates a third plane that is parallel to the second plane and that includes the selected voxel (step 354). The computer calculates the midpoint of the third plane (step 356) and rotates the plane to the orientation that yields the smallest possible cross-sectional area (step 357). The computer continues adding and rotating planes in this manner until the other end of the arch is reached (step 358). The computer identifies the planes at which local minima in cross-sectional area occur and labels these planes as "interproximal planes," which approximate the locations of the interproximal margins (step 360).

Figure 21:
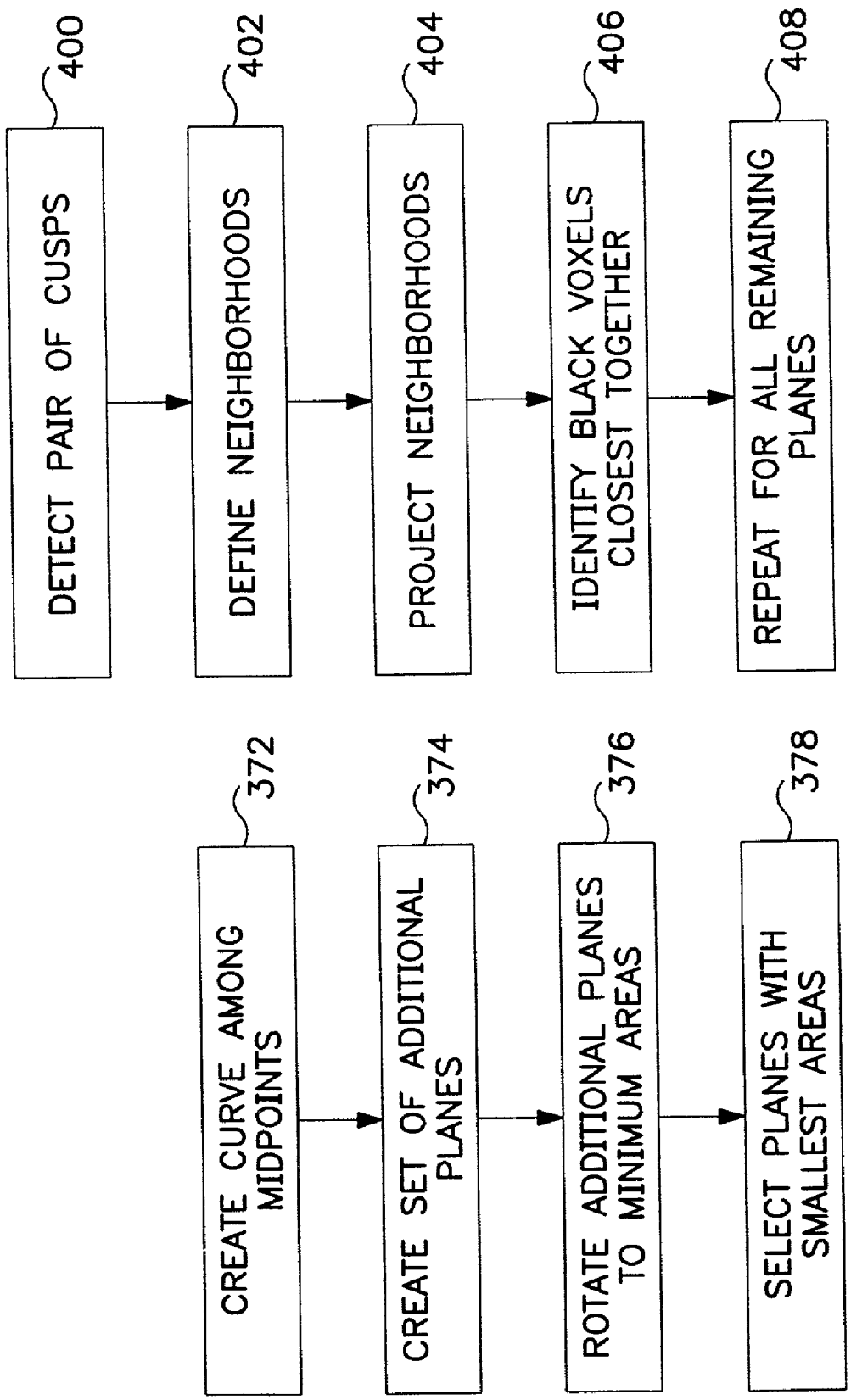

One variation of this technique, described in FIG. 21, allows the computer to refine its identification of interproximal planes by creating additional, more closely positioned planes in areas around the planes labeled as interproximal. The computer first creates a curve that fits among the midpoints of the planes labeled as interproximal planes (step 372) and then creates a set of additional planes along this curve (step 374). The additional planes are not evenly spaced along the curve, but rather are concentrated around the interproximal margins. The planes in each interproximal area are spaced very closely (e.g., 0.05 mm from each other). The computer rotates each of the newly constructed planes about two orthogonal axes until the plane reaches its minimum cross-sectional area (step 376). The computer then selects the plane in each cluster with the smallest cross-sectional area as the plane that most closely approximates the interproximal margin (step 378).

Figure 22:
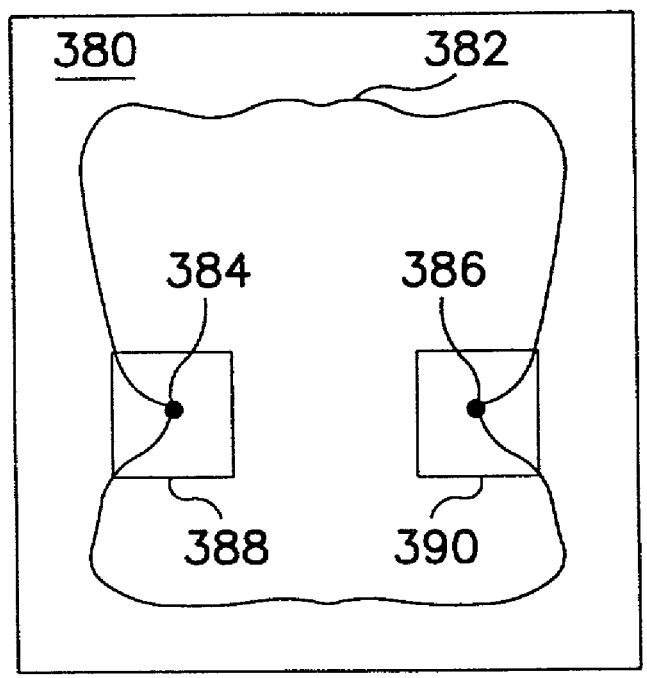
FIG. 22 is a vertical 2D cross-sectional view of a dentition model illustrating the gingival margin detection technique for use in segmenting the dentition model.
Figure 23:
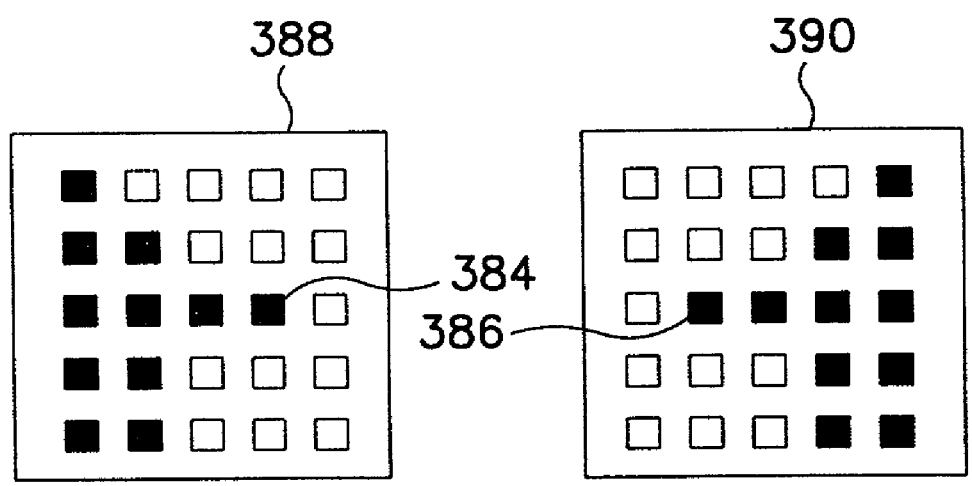
FIG. 23 shows a group of voxels in a 2D slice of a dentition model illustrating a gingival margin detection technique.

FIGS. 22, 23, and 24 illustrate a technique for identifying the gingival margin that defines the boundary between tooth and gum in the patient's dentition. This technique involves the creation of a series of vertical 2D planes 380, or slices, that intersect the dentition model roughly perpendicular to the occlusal plane (see FIG. 19A). The cross-sectional surface 382 of the dentition model in each of these planes 380 includes cusps 384, 386 that represent the gingival margin. The computer identifies the gingival margin by applying one or more of the cusp detection techniques described above.

One technique is very similar to the neighborhood filtered cusp detection technique described above, in that voxel neighborhoods 388, 390 are defined on one of the 2D planes to focus the computer's search for cusps on an adjacent 2D plane. Upon detecting a pair of cusps 384, 386 on one 2D plane (step 400), the computer defines one or more neighborhoods 388, 390 to include a predetermined number of voxels surrounding the pair (step 402). The computer projects the neighborhoods onto an adjacent 2D plane by identifying the voxels on the adjacent plane that correspond to the voxels in the neighborhoods 388, 390 on the original plane (step 404). The computer then identifies the pair of black voxels that lie closest together in the two neighborhoods on the adjacent plane, labeling these voxels as lying in the cusp (step 406). The computer repeats this process for all remaining planes (step 408).

Many of these automated segmentation techniques are even more useful and efficient when used in conjunction with human-assisted techniques. For example, techniques that rely on the identification of the interproximal or gingival margins function more quickly and effectively when a human user first highlights the interproximal or gingival cusps in an image of the dentition model. One technique for receiving this type of information from the user is by displaying a 2D or 3D representation and allowing the user to highlight individual voxels in the display. Another technique allows the user to scroll through a series of 2D cross-sectional slices, identifying those voxels that represent key features such as interproximal or gingival cusps, as in the neighborhood-filtered seed cusp detection technique described above (FIGS. 32, 33, and 34). Some of these techniques rely on user interface tools such as cursors and bounding-box markers.

FIGS. 35A–35F illustrate another technique for separating teeth from gingival tissue in the dentition model. This technique is a human-assisted technique in which the computer displays an image of the dentition model (step 760) and allows a human operator to identify, for each tooth, the gingival margin, or gum line 600, encircling the tooth crown 602 (step 762). Some applications of this technique involve displaying a 3D volumetric image of the dentition model and allowing the user to select, with an input device such as a mouse, the voxels that define the gingival line 600 around each tooth crown 602. The computer then uses the identified gingival line to model the tooth roots and to create a cutting surface that separates the tooth, including the root model, from the gingival tissue 604.

Once the human operator has identified the gingival line 600, the computer selects a point 606 that lies at or near the center of the tooth crown 602 (step 764). One way of choosing this point is by selecting a 2D image slice that is parallel to the dentition's occlusal plane and that intersects the tooth crown 602, and then averaging the x- and y-coordinate values of all voxels in this 2D slice that lie on the surface 608 of the tooth crown 602. After selecting the center point 606, the computer defines several points 605 on the gingival line 600 (step 766) and fits a plane 610 among these points 605 (step 768). The computer then creates a line segment 612 that is normal to the plane 610 and that extends a predetermined distance from the selected center point 606 (step 770). The expected size of a typical tooth or the actual size of the patient's tooth determines the length of the line segment 612. A length on the order of two centimeters is sufficient to model most tooth roots. The computer defines a sphere 614, or a partial sphere, centered at the selected center point 606 (step 772). The radius of the sphere 614 is determined by the length of the line segment 612.

The computer then shifts the plane 610 along the line segment 612 so that the plane 610 is tangential to the sphere 614 (step 774). In some applications, the computer allows the human operator to slide the plane 610 along the surface of the sphere 614 to adjust the orientation of the plane 610 (step 776). This is useful, for example, when the tooth crown 602 is tilted, which suggests that the tooth roots also are tilted. The computer then creates a projection 616 of the gingival line 600 on the shifted plane 610 (step 778). The tooth roots are modeled by creating a surface 618 that connects the gingival line 600 to the projection 616 (step 780). The computer uses this surface as a cutting surface to separate the tooth from the gingival tissue. The cutting surface extends in a direction that is roughly perpendicular to the occlusal surface of the tooth crown 602.

In general, the surface 618 that connects the gingival line 600 to the projection is formed by straight line segments that extend between the gingival line and the projection. However, some implementations allow curvature along these line segments. In some applications, the computer scales the projection 616 to be larger or smaller than the gingival line 600, which gives the surface 618 a tapered shape (step 782). Many of these applications allow the computer, with or without human assistance, to change the profile of the tapered surface so that the rate of tapering changes along the length of the surface 618 (step 784). For example, some surfaces taper more rapidly as distance from the tooth crown increases.

FIGS. 37A–C and 38 illustrate another human-assisted technique for separating teeth from gingival tissue in the dentition model. This technique involves displaying an image of the dentition model to a human operator (step 790) and allowing the operator to trace the gingival lines 620, 622 on the buccal and lingual sides of the dental arch (step 792). This produces two 3D curves 624, 626 representing the gingival lines 620, 622 on the buccal and lingual surfaces. The computer uses these curves 624, 626 to create a 3D cutting surface 628 that separates the tooth crowns 630, 632 from the gingival tissue 634 in the dentition model (step 794). The cutting surface 628 is roughly parallel to the occlusal surface of the tooth crowns 630, 632.

Figure 37A:
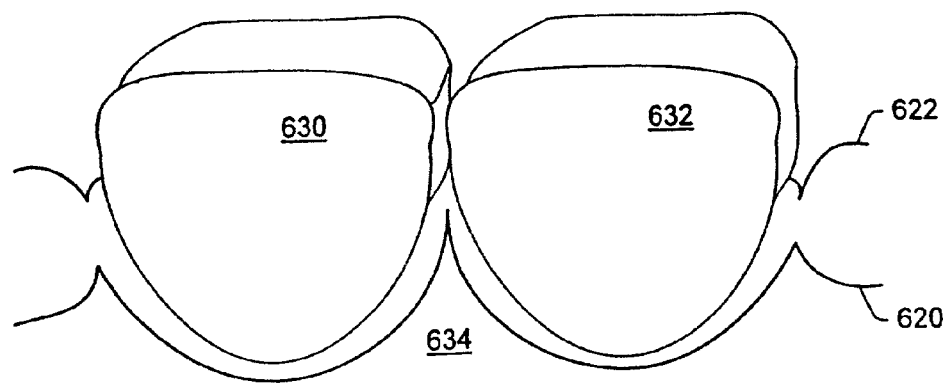
FIGS. 37A, 37B, and 37C illustrate another technique for segmenting a digital dentition model into models of individual teeth.
Figure 37C:
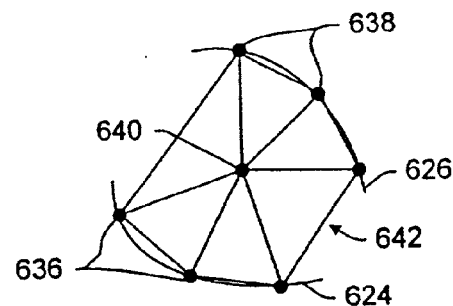
Figure 37B:
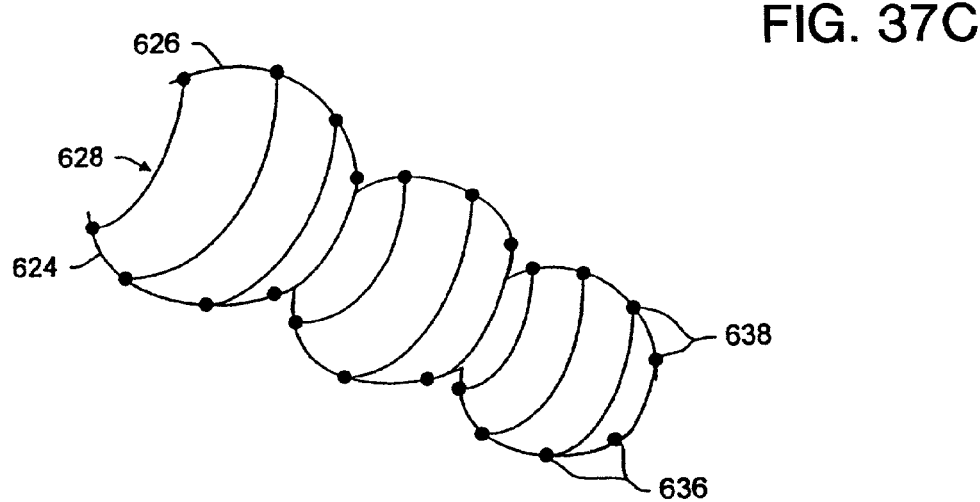
Figures 38, 39:
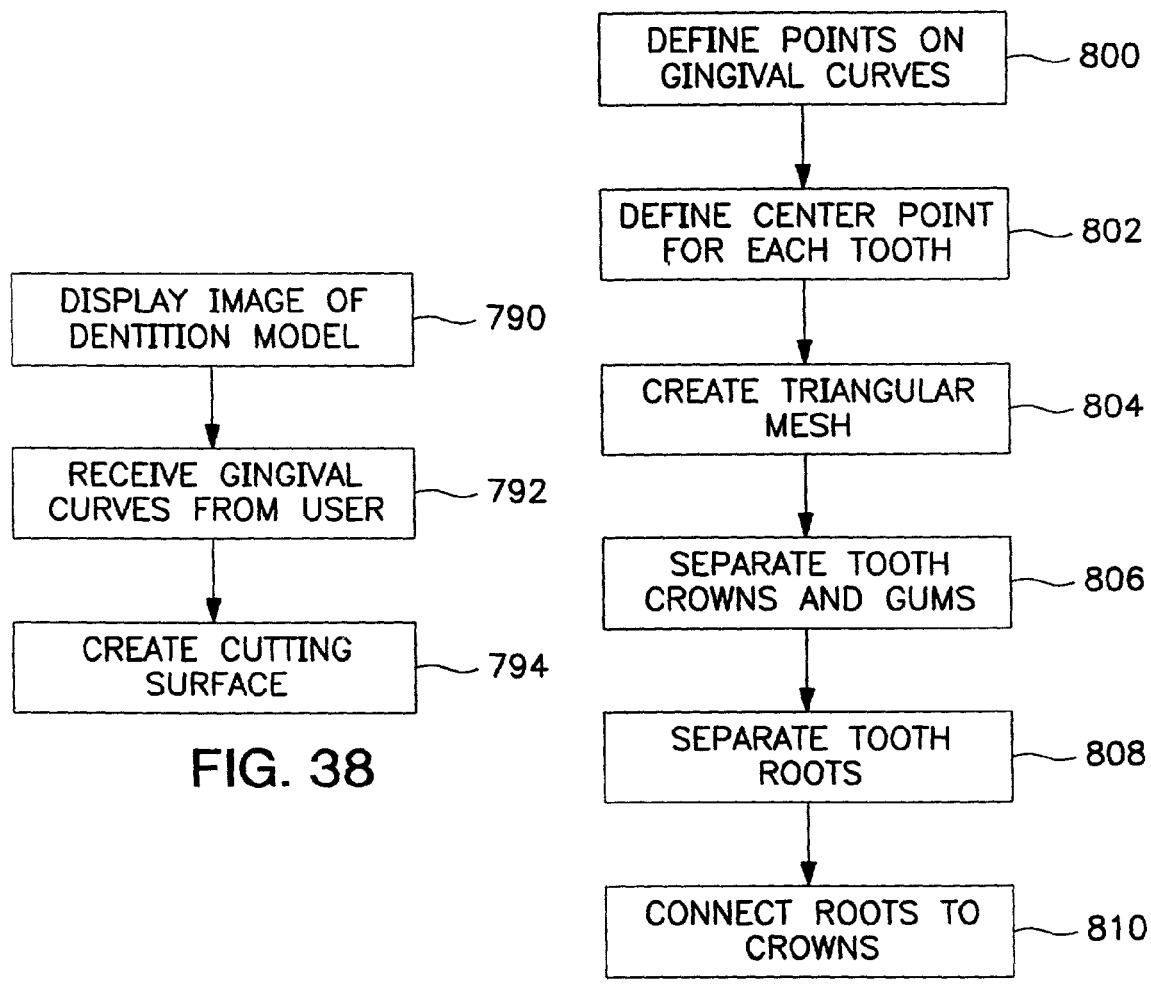
FIGS. 38 and 39 are flowcharts for the technique of FIGS. 37A, 37B, and 37C.

FIGS. 37C and 39 illustrate one technique for defining the cutting surface 628. In general, the computer creates the cutting surface 628 by defining points 636, 638 along each of the 3D curves 624, 626 and defining the cutting surface 628 to fit among the points 636, 638. The computer first defines the points 636, 638 on the 3D curves 624, 626 (step 800) and then defines a point 640 at or near the center of each tooth crown 630 (step 802). One way of defining the center point 640 is by averaging the x-, y-, and z-coordinate values for all of the points 636, 638 lying on the portions of the gingival curves 624, 626 associated with that tooth. The computer then creates a triangular surface mesh 642 using the center point 640 and the points 636, 638 on the gingival curves as vertices (step 804). The computer uses this surface mesh 642 to cut the tooth crowns away from the gingival tissue (step 806). In some implementations, a tooth root model is created for each crown, e.g., by projecting the gingival curves onto a distant plane, as described above (step 808). The computer connects the roots to the crowns to complete the individual tooth models (step 810).

All of the segmentation techniques described above are useful in creating digital models of individual teeth, as well as a model of gingival tissue surrounding the teeth. In some cases, the computer identifies and segments the teeth using one of these techniques to form the individual tooth models, and then uses all remaining data to create the gingival model.

OTHER IMPLEMENTATIONS

In many instances, the computer creates proposals for segmenting the dentition model and then allows the user to select the best alternative. For example, one version of the arch curve fitting technique described above requires the computer to create a candidate catenary or spline curve, which the user is allowed to modify by manipulating the mathematical control parameters. Other techniques involve displaying several surfaces that are candidate cutting surfaces and allowing the user to select the appropriate surfaces.

Some implementations of the invention are realized in digital electronic circuitry, such as an application specific integrated circuit (ASIC); others are realized in computer hardware, firmware, and software, or in combinations of digital circuitry and computer components. The invention is usually embodied, at least in part, as a computer program tangibly stored in a machine-readable storage device for execution by a computer processor. In these situations, methods embodying the invention are performed when the processor executes instructions organized into program modules, operating on input data and generating output. Suitable processors include general and special purpose microprocessors, which generally receive instructions and data from read-only memory and/or random access memory devices. Storage devices that are suitable for tangibly embodying computer program instructions include all forms of nonvolatile memory, including semiconductor memory devices, such as EPROM, EEPROM, and flash memory devices; magnetic disks such as internal hard disks and removable disks; magneto-optical disks; and CD-ROM.

The invention has been described in terms of particular embodiments. Other embodiments are within the scope of the following claims.

What is claimed is:

1. A computer-implemented method for use in manipulating a digital model of a patient's dentition, the method comprising:
   obtaining a three-dimensional (3D) digital model of the patient's dentition; and
   analyzing the digital model in a computer to determine the orientation of at least one axis of the digital model automatically, the analyzing comprising:
      creating an Oriented Bounding Box (OBB) around the digital model and
      identifying a z-axis as extending in a direction in which the OBB has minimum thickness, wherein the z-axis extends from a bottom surface of the digital model to a top surface of the model, and wherein the method includes automatically identifying the top and bottom surfaces of the digital model.

2. The method of claim 1, wherein one of the surfaces is substantially flat and another of the surfaces is textured, and wherein identifying the top and bottom surfaces includes:
creating one or more planes that are roughly normal to the z-axis; and
creating line segments that extend between the one or more planes and the top and bottom surfaces of the digital model.

3. The method of claim 2, wherein identifying the top and bottom surfaces includes identifying the surface for which all of the line segments are of one length as being the flat surface.

4. The method of claim 2, wherein identifying the top and bottom surfaces includes identifying the surface for which the line segments have varying lengths as being the textured surface.

5. The method of claim 1, wherein analyzing the digital model includes selecting a two-dimensional (2D) plane that contains the axis and an arch-shaped cross section of the dentition model and identifying the orientation of the axis in this plane.

6. The method of claim 5, wherein the arch-shaped cross section is roughly symmetrical about the axis.

7. The method of claim 6, wherein analyzing the digital model includes:
identifying a point at each end of the arch-shaped cross section;
creating a line segment that extends between the identified points; and
identifying the orientation of the axis as being roughly perpendicular to the line segment.

8. The method of claim 7, wherein identifying a point at each end of the arch includes:
selecting a point that lies within an area surrounded by the arch-shaped cross section;
creating a line segment that extends between the selected point and an edge of the 2D plane;
sweeping the line segment in a circular manner around the selected point; and
identifying points at the ends of the arch-shaped cross section at which the sweeping line segment begins intersecting the cross section of the digital model and stops intersecting the cross section of the digital model.

9. The method of claim 6, wherein analyzing the dentition model includes identifying the orientation of another axis that is roughly perpendicular to the identified axis.

10. A computer program, stored on a tangible storage medium, for use in manipulating a digital model of a patient's dentition, the program comprising executable instructions that, when executed by a computer, cause the computer to:
obtain a three-dimensional (3D) digital model of the patient's dentition; and
analyze the digital model to determine the orientation of at least one axis of the digital model automatically by:
creating an Oriented Bounding Box (OBB) around the digital model: and
identifying a z-axis as extending in a direction in which the OBB has minimum thickness, wherein the z-axis extends from a bottom surface of the digital model to a top surface of the model, and wherein the computer automatically identifies the top and bottom surfaces of the digital model.

11. The program of claim 10, wherein one of the surfaces is substantially flat and another of the surfaces is textured, and wherein, in identifying the top and bottom surfaces, the computer program:
creates one or more planes that are roughly normal to the z-axis; and
creates line segments that extend between the one or more planes and the top and bottom surfaces of the digital model.

12. The program of claim 11, wherein, in identifying the top and bottom surfaces, the computer program identifies the surface for which all of the line segments are of one length as being the flat surface.

13. The program of claim 11, wherein, in identifying the top and bottom surfaces, the computer program identifies the surface for which the line segments have varying lengths as being the textured surface.

14. The program of claim 10, wherein, in analyzing the digital model, the computer selects a two-dimensional (2D) plane that contains the axis and an arch-shaped cross section of the dentition model and identifying the orientation of the axis in this plane.

15. The program of claim 14, wherein the arch-shaped cross section is roughly symmetrical about the axis.

16. The program of claim 15, wherein, in analyzing the digital model, the computer program:
identifies a point at each end of the arch-shaped cross section;
creates a line segment that extends between the identified points; and
identifies the orientation of the axis as being roughly perpendicular to the line segment.

17. The program of claim 16, wherein, in identifying a point at each end of the arch, the computer program:
selects a point that lies within an area surrounded by the arch-shaped cross section;
creates a line segment that extends between the selected point and an edge of the 2Plane;
sweeps the line segment in a circular manner around the selected point; and
identifies points at the ends of the arch-shaped cross section at which the sweeping line segment begins intersecting the cross section of the dentition model and stops intersecting the cross section of the digital model.

18. The program of claim 15, wherein, in analyzing the digital model, the computer identifies the orientation of another axis that is roughly perpendicular to the identified axis.

* * * * *